United States Patent
Nakayama et al.

(10) Patent No.: US 11,098,074 B2
(45) Date of Patent: Aug. 24, 2021

(54) CHIRAL TETRADENTATE LIGAND, METHOD FOR PRODUCING SAME AND TRANSITION METAL COMPLEX OF SAID CHIRAL TETRADENTATE LIGAND

(71) Applicant: TAKASAGO INTERNATIONAL CORPORATION, Tokyo (JP)

(72) Inventors: Yuji Nakayama, Kanagawa (JP); Naota Yokoyama, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 16/967,951

(22) PCT Filed: Feb. 6, 2019

(86) PCT No.: PCT/JP2019/004309
§ 371 (c)(1),
(2) Date: Aug. 6, 2020

(87) PCT Pub. No.: WO2019/156134
PCT Pub. Date: Aug. 15, 2019

(65) Prior Publication Data
US 2020/0369700 A1    Nov. 26, 2020

(30) Foreign Application Priority Data
Feb. 9, 2018   (JP) .............................. JP2018-021749

(51) Int. Cl.
C07F 15/00   (2006.01)
C07F 15/02   (2006.01)
C07F 9/6558  (2006.01)

(52) U.S. Cl.
CPC ........ C07F 15/025 (2013.01); C07F 9/65583 (2013.01); C07F 15/0053 (2013.01)

(58) Field of Classification Search
CPC .................................................. C07F 15/025
See application file for complete search history.

(56) References Cited

U.S. PATENT DOCUMENTS

| | | | |
|---|---|---|---|
| 2016/0107151 A1 | 4/2016 | Saito et al. | |
| 2019/0127407 A1 | 5/2019 | Nakayama et al. | |

FOREIGN PATENT DOCUMENTS

| | | |
|---|---|---|
| CN | 103980317 A | 8/2014 |
| WO | 2014/136795 A1 | 9/2014 |
| WO | 2017/170952 A1 | 10/2017 |

OTHER PUBLICATIONS

International Search Report (PCT/ISA/210) issued by the International Searching Authority in International Application No. PCT/JP2019/004309, dated Apr. 16, 2019.
Written Opinion (PCT/ISA/237) issued by the International Searching Authority in International Application No. PCT/JP2019/004309, dated Apr. 16, 2019.
Kristina Wilckens et al., "Chiral 1,1' -Bi(tetrahydroisoquinoline)-Type Diamines as Efficient Ligands for Nickel-Catalysed Enantioselective Michael Addition to Nitroalkenes", European Journal of Organic Chemistry, 2011, pp. 5441-5446 (6 pages total).
Khong Duc Thinh et al., "Efficient Direct and Modular Stereoselective Synthesis of Highly Functionalized Tetrahydroisoquinolines and C2-1,1'-Bitetrahydroisoquinolines", Synthesis, 2014, vol. 46, pp. 2780-2788 (10 pages total).
Christine Sui-Seng et al., "Highly Efficient Catalyst Systems Using Iron Complexes with a Tetradentate PNNP Ligand for the Asymmetric Hydrogenation of Polar Bonds", Angewandte Chemie International Edition, 2008, vol. 47, No. 5, pp. 940-943 (4 pages total).
Weiwei Zuo et al., "Amine(imine)diphosphine Iron Catalysts for Asymmetric Transfer Hydrogenation of Ketones and Imines", Science, Nov. 29, 2013, vol. 342, pp. 1080-1083 (5 pages total).
Raphael Bigler et al., "Iron(II)/(NH)$_2$ P$_2$ Macrocycles: Modular, Highly Enantioselective Transfer Hydrogenation Catalysts", ACS Catalysis, Aug. 23, 2016, vol. 6, pp. 6455-6464 (10 pages total).
Alexandre A. Mikhailine et al., "The Mechanism of Efficient Asymmetric Transfer Hydrogenation of Acetophenone Using an Iron(11)Complex Containing an (S,S)-Ph$_2$PCH$_2$CH=NCHPhCHPhN=CHCH$_2$PPh$_2$ Ligand: Partial Ligand Reduction Is the Key", Journal of the American Chemical Society, 2012, vol. 134, No. 29, pp. 12266-12280 (15 pages total).

*Primary Examiner* — Benjamin J Packard
(74) *Attorney, Agent, or Firm* — Sughrue Mion, PLLC

(57) ABSTRACT

The present invention relates to a compound represented by the formula ($1^A$). G represents a group selected from the group consisting of a monovalent group represented by the formula ($G^P$) and a monovalent group represented by the formula ($G^S$). $R^4$, $R^5$, $R^6$, $R^7$, $R^8$, $R^9$, $R^{10}$, $R^{11}$, and $R^{12}$ each independently represent a hydrogen atom or a group selected from the group consisting of an alkyl group, an alkenyl group, an aryl group, an aralkyl group, an alkoxy group, a halogeno group, and a halogeno alkyl group.

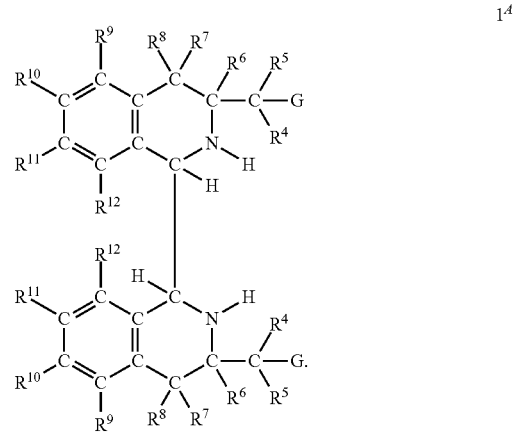

8 Claims, No Drawings

CHIRAL TETRADENTATE LIGAND, METHOD FOR PRODUCING SAME AND TRANSITION METAL COMPLEX OF SAID CHIRAL TETRADENTATE LIGAND

CROSS REFERENCE TO RELATED APPLICATIONS

This application is a National Stage of International Application No. PCT/JP2019/004309, filed Feb. 6, 2019, claiming priority based on Japanese Patent Application No. 2018-021749, filed Feb. 9, 2018, the contents of all of which are incorporated herein by reference in their entirety.

TECHNICAL FIELD

The present invention relates to a new chiral tetradentate ligand and a production method therefor, and a transition metal complex thereof.

BACKGROUND ART

Today, various metal complexes including an organic compound containing a group having a lone electron pair (i.e. coordinating group) capable of coordinating to a metal species, namely a ligand and various metal species, particularly a transition metal complex, are energetically used as a catalyst in an organic synthesis reaction. It is known that not only a metal species but also a ligand plays an extremely important role as a factor of exhibiting the performance and activity of the catalyst described above.

Among these ligands, an organic compound having four coordinating groups (i.e. tetradentate ligand) forms three or more chelate rings at the time of coordination to a metal atom and therefore has a characteristic such that its metal complex is highly stabilized. In the metal complex having an octahedral structure, since the tetradentate ligand can be coordinated not only in the trans fashion but also in the cis-α/cis-β fashion, a new asymmetric environment can be induced in a metal center of the complex. Further, a tetradentate ligand having been introduced various asymmetric environments such as asymmetric carbon atoms and axial chirality (i.e. chiral tetradentate ligand) can be applied as a ligand for various asymmetric catalytic reactions. Therefore, the tetradentate ligand has a high value from not only academic but also industrial viewpoints. As described above, since the tetradentate ligand exhibits very interesting behavior, the tetradentate ligand occupies an important position in the fields of complex chemistry, catalyst chemistry, and organic synthetic chemistry, and researches and developments are still actively conducted at present.

The structures of the tetradentate ligand reported so far are extended from a simple one capable of being synthesized in a short process to a complicated one requiring a multistage reaction, but from the industrial viewpoint, a tetradentate ligand which is easy to synthesis at large-scale is preferred. Among them, it has been reported that the chiral tetradentate ligand having two coordinating phosphorus atoms and two coordinating nitrogen atoms in the structure (i.e. chiral $P_2N_2$ tetradentate ligand) can stabilize an unstable metal species such as a low-valent iron compound, and a complex thereof exhibits excellent catalytic activity in an industrially important reaction such as an asymmetric hydrogenation reaction or an asymmetric transfer hydrogenation reaction.

Examples of such a chiral $P_2N_2$ tetradentate ligand include a dehydrative condensate of 2-diphenylphosphinobenzaidehyde and an optically active ethylenediamine derivative. It has been reported that the chiral $P_2N_2$ tetradentate ligand can be synthesized conveniently and stabilize the low-valent iron compounds, and that the iron complex thereof exhibits high catalytic activity in the asymmetric hydrogenation reaction or the asymmetric transfer hydrogenation reaction of ketones (Non-Patent Literature 1: Ligand (NP-1). With this report as a pioneering figure, chiral. $P_2N_2$ tetradentate ligands having an asymmetric structure or a macrocyclic structure have been energetically studied, and it has been reported that iron complexes thereof have extremely excellent catalytic activity and asymmetric induction ability in the asymmetric transfer hydrogenation reaction of ketones (Non-Patent Literature 2: Ligand (NP-2) and Non-Patent Literature 3: Ligand (NP-3)). Hereinafter, FIG. 1 shows structures of these chiral $P_2N_2$ tetradentate ligands (NP-1) to (NP-3).

[Chem. 1]

FIG. 1

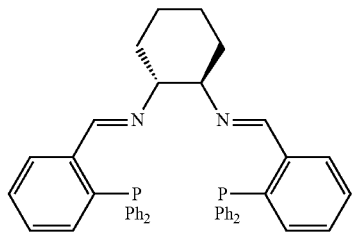

NP-1

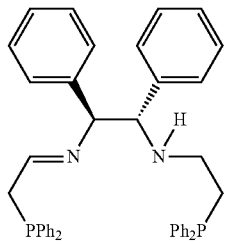

NP-2

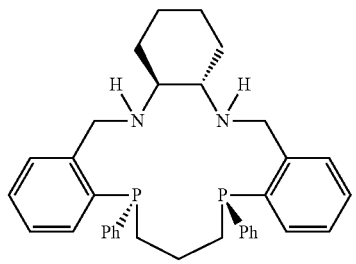

NP-3

CITATION LIST

Non-Patent Literature

Non-Patent Literature 1: Christine Sui-Seng, Friederike Freutel, Alan J. Lough, Robert H. Morris, Angew. Chem. Int. Ed., 2008, 47, 940.

Non-Patent Literature 2: WeiWei Zuo, Alan J. Lough, Young Feng Li, Robert H. Morris, Science, 2013, 342, 1080.

Non-Patent Literature 3: Raphael Bigler, Rafael Huber, Marco Stockli, Antonio Mezzetti, ACS Catal., 2016, 6, 6455.

SUMMARY OF INVENTION

Technical Problem

In Non-Patent Literature 1, a chiral $P_2N_2$ tetradentate ligand (NP-1) having a simple structure that can be easily synthesized is reported. However, asymmetric induction ability of the iron complex thereof is not sufficient, and in the asymmetric transfer hydrogenation reaction of acetophenone using the iron complex as a catalyst, optical purity of a product remains only 30% ee. On the other hand, in Non-Patent Literature 2 and Non-Patent Literature 3, it has been reported that chiral $P_2N_2$ tetradentate ligands having an asymmetric structure or a macrocyclic structure (i.e. ligand (NP-2)/ligand (NP-3)) show greatly improved asymmetric induction ability of the iron complexes thereof. For example, by using the iron complexes as a catalyst in the reaction described above, optical purity of a product reaches up to 99% ee. However, since the chiral $P_2N_2$ tetradentate ligands have an asymmetric or a macrocyclic structure, there is a problem that synthesis is extremely complicated and scaling up is difficult. Although it is not limited to such a chiral $P_2N_2$ tetradentate ligand, as a problem in development of a practical ligand, it is possible to mention both performance (in particular, stabilization of unstable metal species and asymmetric induction ability) and ease of synthesis.

The present invention has been made in view of the above situation. That is, an object of the present invention is to provide a chiral tetradentate ligand in which a transition metal complex thereof exhibits excellent performance and a convenient and efficient method for producing such a chiral tetradentate ligand.

Solution to Problem

As a result of intensive studies to solve the above problems, the present inventors have found out that a new chiral $P_2N_2$ tetradentate ligand can be synthesized conveniently in good yield by reacting a secondary phosphine or a secondary phosphine-boron trihydride complex where various derivatives are available with intermediates that can be easily synthesized from 4-benzyl-2-oxazolidinone. It has been found that the chiral $P_2N_2$ tetradentate ligand is coordinated to a low-valent iron compound which tends to be easily oxidized to give a stable iron complex in air, and the iron complex exhibits high asymmetric induction ability in the asymmetric transfer hydrogenation reaction of ketones. It has also been thud out that the ruthenium complex of the chiral $P_2N_2$ tetradentate ligand exhibits excellent catalytic activity in the hydrogenation reaction of esters and the asymmetric hydrogenation reaction of ketones. In addition, it has also been found out that by applying this technique, a new ligand in which two phosphorus atoms in the chiral tetradentate ligand are replaced with two sulfur atoms (i.e. chiral $S_2N_2$ tetradentate ligand) can be synthesized, and the chiral $S_2N_2$ ligand exhibits excellent performance in the asymmetric hydrogenation reaction of ketones. The present inventors have completed the present invention by proceeding further studies based on these fundamental knowledge.

That is, the present invention includes the following [1] to [8].

[1] A compound represented by the following general formula ($1^A$)

[Chem. 2]

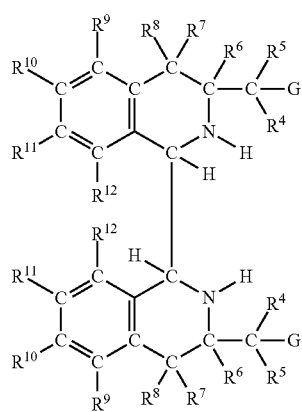

[wherein in the formula ($1^A$), a solid line represents a single bond, and a double line represents a double bond; C represents a carbon atom, H represents a hydrogen atom, and N represents a nitrogen atom; G represents a group selected from the group consisting of a monovalent group represented by the following general formula ($G^P$)

[Chem. 3]

(wherein in the formula ($G^P$), a solid line represents a single bond, a broken line represents a coordinate bond, and a solid line intersected with a wavy line represents a bond to a carbon atom; P represents a phosphorus atom; $BH_3$ represents boron trihydride; A subscript n represents a coordination number of $BH_3$ to P and indicates an integer value of 0 or 1; $R^1$ and $R^2$ each independently represent a group selected from the group consisting of an alkyl group, a cycloalkyl group, an alkenyl group which may have a substituent, an aryl group which may have a substituent, a heteroaryl group which may have a substituent, and an aralkyl group which may have a substituent; $R^1$ and $R^2$ may bond to each other to form a ring which may have a substituent) and a monovalent group represented by the following general formula ($G^S$)

[Chem. 4]

(wherein in the formula ($G^S$), a solid line represents a single bond, and a solid line intersected with a wavy line represents a bond to a carbon atom; S represents a sulfur atom; $R^3$ represents a group selected from the group consisting of an alkyl group, an alkenyl group which may have a substituent, an aryl group which may have a substituent, a heteroaryl group which may have a substituent, and an aralkyl group which may have a substituent); $R^4$, $R^5$, $R^6$, $R^7$, $R^8$, $R^9$, $R^{10}$, $R^{11}$, and $R^{12}$ each independently represent a hydrogen atom or a group selected from the group consisting of an alkyl group, an alkenyl group, an aryl group, an aralkyl group, an alkoxy group, a halogeno group, and a halogenoalkyl group].

[2] The compound according to the above [1], wherein all of the $R^4$ to $R^{12}$ are hydrogen atoms.

[3] The compound according to the above [1] or [2], wherein G is $G^P$.

[4] The compound according to any one of the above [1] to [3], which is an optically active substance.

[5] A method for producing the compound according to any one of the above [1] to [4], including reacting a compound represented by the following general formula ($2^A$)

[Chem. 5]

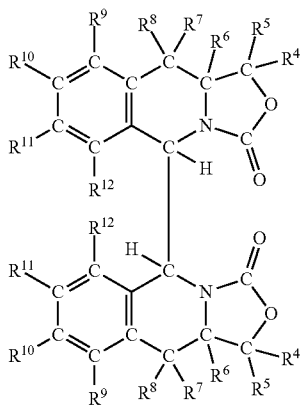

(wherein in the formula (2$^A$), a solid line represents a single bond and a double line represents a double bond; C represents a carbon atom, H represents a hydrogen atom, N represents a nitrogen atom, and O represents an oxygen atom; $R^4$, $R^5$, $R^6$, $R^7$, $R^8$, $R^9$, $R^{10}$, $R^{11}$, and $R^{12}$ each independently represent a hydrogen atom or a group selected from the group consisting of an alkyl group, an alkenyl group, an aryl group, an aralkyl group, an alkoxy group, a halogeno group, and a halogeno alkyl group) with a compound represented by the following general formula (3)

[Chem. 6]

H—G              3

(wherein in the formula (3), a solid line represents a single bond; H represents a hydrogen atom; G represents a group same as G defined in the above [1]).

[6] A transition metal complex having the compound according to any one of the above [1] to [4] as a ligand.

[7] The transition metal complex according to the above [6], wherein a metal species is a metal species selected from the group consisting of transition metals of Group 8 to 11.

[8] The transition metal complex according to the above [7], wherein the metal species is a metal species selected from transition metals of Group 8.

Advantageous Effects of Invention

The new compound of the present invention represented by the general formula (1$^A$) (hereinafter, referred to as a compound (1$^A$) of the present invention) can be synthesized conveniently by reacting a compound represented by the general formula (2$^A$) (hereinafter, referred to as an intermediate (2$^A$)) with a compound represented by the general formula (3). Further, a transition metal complex having the compound (1$^A$) of the present invention as a ligand (hereinafter, referred to as a transition metal complex of the present invention) exhibits excellent catalytic activity in various organic synthesis reactions. For example, the iron complex of the compound (1$^A$) of the present invention exhibits excellent asymmetric induction ability in the asymmetric transfer hydrogenation reaction of ketones, and the ruthenium complex of the compound (1$^A$) of the present invention exhibits high catalytic activity in the hydrogenation reaction of esters and the asymmetric hydrogenation reaction of ketones. By these reactions, it is possible to efficiently produce primary alcohols and optically active secondary alcohols that have an industrially high value.

DESCRIPTION OF EMBODIMENTS

With Respect to Compound (1$^A$) of the Present Invention

First, the compound (1$^A$) of the present invention is described in detail. In the general formula (1$^A$), a solid line represents a single bond, and a double line represents a double bond. C represents a carbon atom, H represents a hydrogen atom, and N represents a nitrogen atom. G represents a group selected from the group consisting of monovalent groups represented by the general formulae (G$^P$) and (G$^S$). In the general formulae (G$^P$) and (G$^S$), a solid line represents a single bond, a broken line represents a coordinate bond, and a solid line intersected with a wavy line represents a bond to a carbon atom. P represents a phosphorus atom, and S represents a sulfur atom. BH$_3$ represents boron trihydride. A subscript a represents a coordination number of BH$_3$ to P and indicates an integer value of 0 or 1. $R^1$, $R^2$, and $R^3$ each independently represent a group selected from the group consisting of an alkyl group, a cycloalkyl group, an alkenyl group which may have a substituent, an aryl group which may have a substituent, a heteroaryl group which may have a substituent, and an aralkyl group which may have a substituent, preferably represent a group selected from the group consisting of an alkyl group, a cycloalkyl group, and an aryl group which may have a substituent. $R^4$, $R^5$, $R^6$, $R^7$, $R^8$, $R^9$, $R^{10}$, $R^{11}$, and $R^{12}$ independently represent a hydrogen atom or a group selected from the group consisting of an alkyl group, an alkenyl group, an aryl group, an aralkyl group, an alkoxy group, a halogeno group, and a halogenoalkyl group, preferably represent a hydrogen atom.

The alkyl groups of $R^1$ to $R^3$ may be linear or branched, and examples thereof include an alkyl group having 1 to 30 carbon atoms, preferably an alkyl group having 1 to 20 carbon atoms, and more preferably an alkyl group having 1 to 10 carbon atoms, and specific examples thereof include a methyl group, an ethyl group, an n-propyl group, a 2-propyl group, an n-butyl group, a 2-butyl group, an isobutyl group, a tert-butyl group, an n-pentyl group, a 2-pentyl group, a 3-pentyl group, a 2-methylbutyl group, a 3-methylbutyl group, a 2-methylbutan-2-yl group, a 2-methylbutan-3-yl group, a 2,2-dimethylpropyl group, an n-hexyl group, a 2-hexyl group, a 3-hexyl group, a 2-methylpentyl group, a 3-methylpentyl group, a 4-methylpentyl group, a 2-methylpentan-2-yl group, a 2-methylpentan-3-yl group, a 2-methylpentan-4-yl group, a 3-methylpentan-2-yl group, a 3-methylpentan-3-yl group, a 2,2-dimethylbutyl group, a 3,3-dimethylbutyl group, a 2,2-dimethylbutan-3-yl group, an n-heptyl group, an n-octyl group, an n-nonyl group, and an n-decyl group, preferable specific examples thereof include an ethyl group and a tert-butyl group.

The cycloalkyl group of $R^1$ to $R^3$ may be monocyclic or polycyclic, and examples thereof include a cycloalkyl group having 3 to 30 carbon atoms, preferably a cycloalkyl group having 3 to 20 carbon atoms, and more preferably a cycloalkyl group having 3 to 10 carbon atoms, specific examples thereof include a cyclopropyl group, a cyclobutyl group, a cyclopentyl group, a cyclohexyl group, a 1-adamantyl group, and a 2-adamantyl group, and a preferable specific example is a cyclohexyl group.

The alkenyl group of $R^1$ to $R^3$ may be linear or branched or cyclic, and examples thereof include an alkenyl group having 2 to 20 carbon atoms, preferably an alkenyl group having 2 to 14 carbon atoms, and more preferably an alkenyl group having 2 to 8 carbon atoms, and specific examples thereof include a vinyl group, a 1-propenyl group, a 2-propenyl group, an allyl group, a 1-cyclohexenyl group, a 1-styryl group, and a 2-styryl group.

Examples of the aryl group of $R^1$ to $R^3$ include an aryl group having 6 to 18 carbon atoms, preferably an aryl group having 6 to 14 carbon atoms, and more preferably an aryl group having 6 to 10 carbon atoms, specific examples thereof include a phenyl group, a 1-naphthyl group, and a 2-naphthyl group, and a preferable specific example is a phenyl group.

Examples of the heteroaryl group of $R^1$ to $R^3$ include heteroaryl groups derived from a 5-membered aromatic heterocycle containing an oxygen atom or a sulfur atom and from a polycyclic aromatic heterocycle formed by ring-fusing the aromatic heterocycle with the aryl group above, and specific examples thereof include a 2-furyl group, a 3-furyl group, a 2-thienyl group, a 3-thienyl group, a 2-benzofuryl group, a 3-benzofuryl group, a 2-benzothienyl group, and a 3-benzothienyl group.

Examples of the aralkyl group of $R^1$ to $R^3$ include an aralkyl group formed by substituting at least one hydrogen atom on the alkyl group or the cycloalkyl group above with the aryl group above, and a polycyclic aralkyl group formed by ring-fusing the cycloalkyl group above with the aryl group above, and specific examples thereof include a benzyl group, a 1-phenylethyl group, a 2-phenylethyl group, a 1-phenylpropyl group, a 2-phenylpropyl group, a 3-phenyipropyl group, a 1-phenyl-2-propyl group, a 2-phenyl-2-propyl group, a 1-indanyl group, a 2-indanyl group, and a 9-fluorenyl group.

$R^1$ and $R^2$ may bond to each other to form a ring which may have a substituent. Specific examples of the ring include a phosphorane ring, a 1H-phosphole ring, a phosphinane ring, a 1,2-dihydrophosphinine ring, a phosphepane ring, and a 1H-phosphepine ring.

Examples of the substituent which may be substituted on the alkenyl group, the aryl group, the heteroaryl group, and the aralkyl group in $R^1$ to $R^3$ and on the ring containing a phosphorus atom formed by combining $R^1$ and $R^2$ with each other include an alkyl group, a cycloalkyl group, an aryl group, an aralkyl group, an alkoxy group, a halogeno group, and a halogenoalkyl group. Among these substituents, examples of the alkyl group, the cycloalkyl group, the aryl group, and the aralkyl group include the groups same as the groups described in detail in description of $R^1$ to $R^3$.

Examples of the alkoxy group as the substituents include an alkoxy group having 1 to 12 carbon atoms, preferably an alkoxy group having 1 to 8 carbon atoms, and more preferably an alkoxy group having 1 to 4 carbon atoms, and specific examples thereof include a methoxy group, an ethoxy group, a 1-propoxy group, a 2-propoxy group, a 1-butoxy group, a 2-butoxy group, and a tert-butoxy group.

Examples of the halogeno group as the substituents specifically include a fluoro group, a chloro group, a bromo group, and an iodo group.

Examples of the halogenoalkyl group as the substituents include a group formed by substituting at least one hydrogen atom on the alkyl group above by a halogen atom, and specific examples thereof include a trifluoromethyl group, a chloromethyl group, and a nonafluorobutyl group.

The alkyl group of $R^4$ to $R^{12}$ may be linear or branched, and examples thereof include an alkyl group having 1 to 12 carbon atoms, preferably an alkyl group having 1 to 8 carbon atoms, and more preferably an alkyl group having 1 to 4 carbon atoms, and specific examples thereof include a methyl group, an ethyl group, an n-propyl group, a 2-propyl group, an n-butyl group, a 2-butyl group, an isobutyl group, and a tert-butyl group.

The alkenyl group of $R^4$ to $R^{12}$ may be linear or branched, and examples thereof include an alkenyl group having 2 to 12 carbon atoms, preferably an alkenyl group having 2 to 8 carbon atoms, and more preferably an alkenyl group having 2 to 4 carbon atoms, and specific examples thereof include a vinyl group, a 1-propenyl group, a 2-propenyl group, and an allyl group.

Examples of the aryl group of $R^4$ to $R^{12}$ include an aryl group having 6 to 18 carbon atoms, preferably an aryl group having 6 to 14 carbon atoms, more preferably an aryl group having 6 to 10 carbon atoms, and specific examples thereof include a phenyl group, a 1-naphthyl group, and a 2-naphthyl group.

Examples of the aralkyl group of $R^4$ to $R^{12}$ include an aralkyl group formed by substituting at least one hydrogen atom on the alkyl group by the aryl group above, and specific examples thereof include a benzyl group, a 1-phenylethyl group and a 2-phenylethyl group.

Examples of the alkoxy group of $R^4$ to $R^{12}$ include an alkoxy group having 1 to 12 carbon atoms, preferably an alkoxy group having 1 to 8 carbon atoms, and more preferably an alkoxy group having 1 to 4 carbon atoms, and specific examples thereof include a methoxy group, an ethoxy group, a 1-propoxy group, a 2-propoxy group, a 1-butoxy group, a 2-butoxy group, and a tert-butoxy group.

Examples of the halogeno group of $R^4$ to $R^{12}$ specifically include a fluoro group, a chloro group, a bromo group, and an iodo group.

Examples of the halogenoalkyl group of $R^4$ to $R^2$ include a group formed by substituting at least one hydrogen atom on the alkyl group above by a halogen atom, and specific examples thereof include a trifluoromethyl group, a chloromethyl group, and a nonaftuorobutyl group.

The compound ($1^A$) of the present invention may be an optically active substance. Specific examples of a preferable form of the compound ($1^A$) of the present invention include a compound represented by the Mowing general formula ($1^B$) (hereinafter, referred to as a compound ($1^B$)) in which all of the $R^4$ to $R^{12}$ in the general formula ($1^A$) are hydrogen atoms.

[Chem. 7]

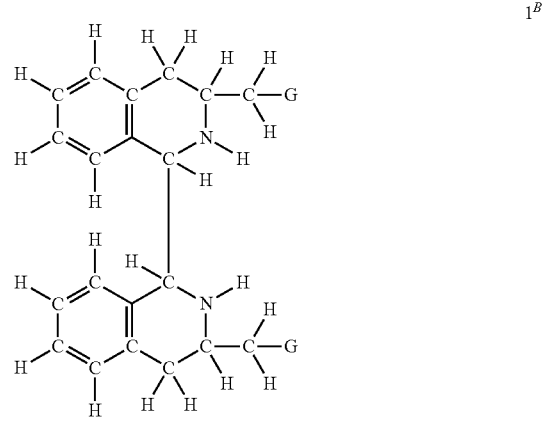

$1^B$ (wherein in the formula ($1^B$), a solid line, a double line, C, N, and G are the same as the solid line, the double line, C, H, N, and G defined in the general formula ($1^A$)).

Specific particularly preferable forms of the compound ($1^A$) of the present invention include as compound ($(S,S,S,S)$-$1^B$-1) to a compound ($S,S,S,S$)-$1^B$-6) shown below.
[Chem. 8]
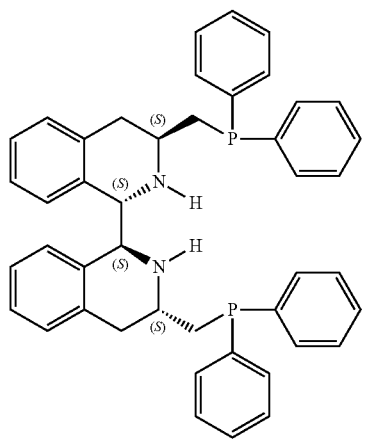
($S,S,S,S$)-$1^B$-1
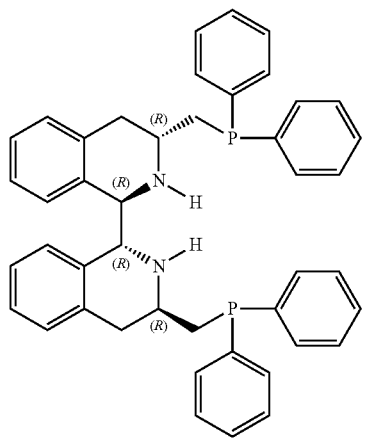
($R,R,R,R$)-$1^B$-1
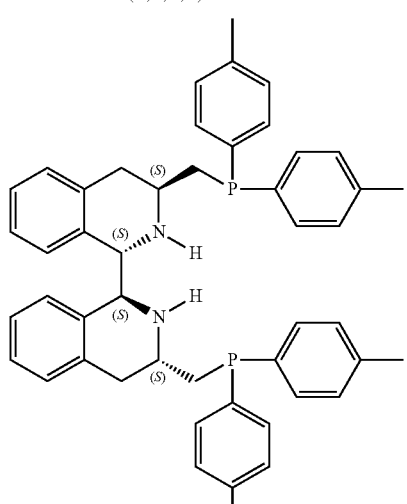
($S,S,S,S$)-$1^B$-2
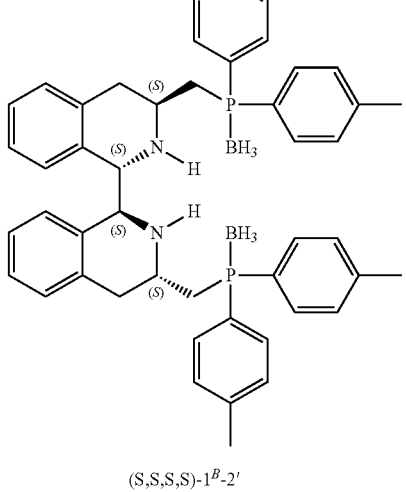
($S,S,S,S$)-$1^B$-2'
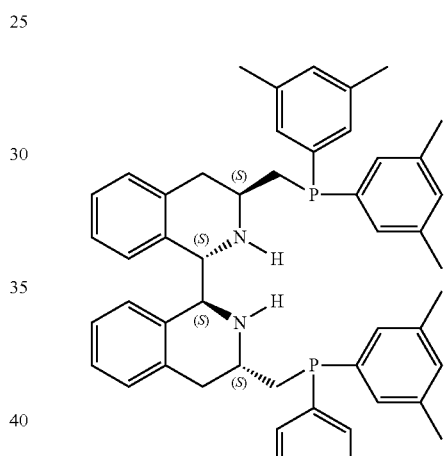
($S,S,S,S$)-$1^B$-3
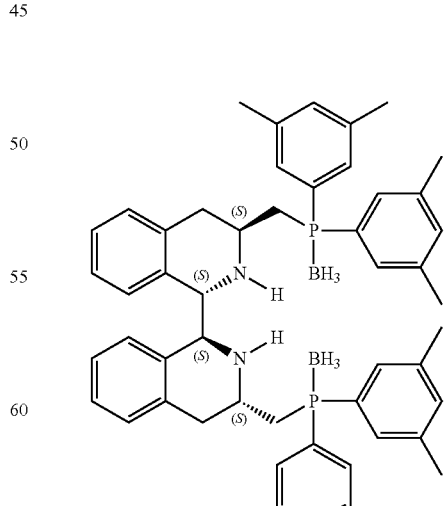
($S,S,S,S$)-$1^B$-3'

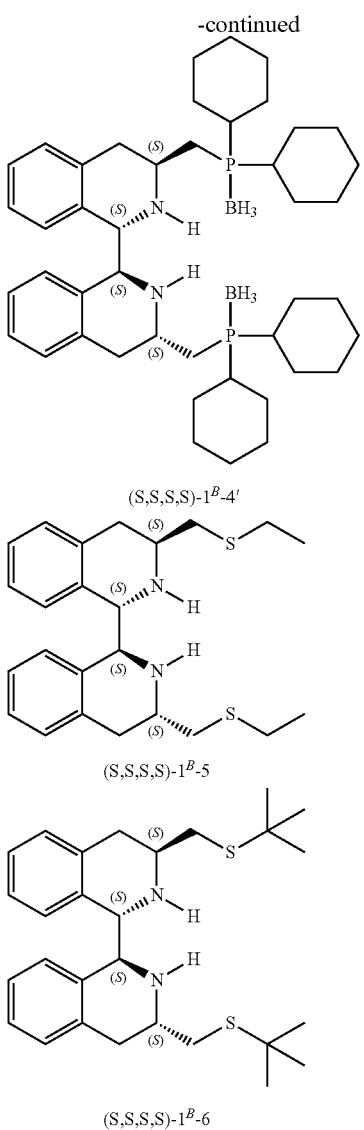

(S,S,S,S)-1$^B$-4′

(S,S,S,S)-1$^B$-5

(S,S,S,S)-1$^B$-6

Since the compound (1$^A$) of the present invention includes a compound that is unstable to air and a compound that is a highly viscous liquid substance and that is difficult to be purified or measured, the compounds may be diluted with a solvent to facilitate handling, or may be reacted with Bronsted acid, specifically a perchloric acid, nitric acid, sulfuric acid, tetrafluoroboric acid, hexafluorophosphoric acid, hydrohalic acid, sulfonic acid, carboxylic acid, and phenols to form a corresponding salt.

Among these, specific examples of the hydrohalic acid include hydrofluoric acid, hydrochloric acid, hydrobromic acid, and hydriodic acid. Specific examples of the sulfonic acid include methanesulfonic acid, trifluoromethanesulfonic acid, p-toluenesulfonic acid, and 10-camphorsultonic acid. Specific examples of the carboxylic acid include formic acid, acetic acid, trifluoroacetic acid, benzoic acid, salicylic acid, oxalic acid, and tartaric acid. Specific examples of the phenols include phenol, p-cresol, p-nitrophenol and pentafluorophenol.

When the Bronsted acid salt of the compound (1$^A$) of the present invention is used for production of the transition metal complex of the present invention, the Bronsted acid salt may be used in a reaction as it is, or may be used after being treated with a base outside a reaction system to liberate the compound (1$^A$) of the present invention, or may be used while liberating the compound (1$^A$) of the present invention by treating with a base in the reaction system.

In a case where the (1$^A$) of the present invention contains boron trihydride, when the compound is used for producing the transition metal complex of the present invention, the compound may be used as it is, or may be used in a reaction after dissociation of boron trihydride outside the reaction system, or may be used while dissociating the boron trihydride in the reaction system. A dissociating agent is preferably used in combination in the dissociation of the boron trihydride, specific examples of such a dissociating agent include a tetrafluoroboric acid-dimethyl ether complex/aqueous solution of sodium hydrogen carbonate, diethylamine, triethylamine, morpholine, and 1,4-diazabicyclo[2,2,2]octane, and preferable specific examples thereof include 1,4-diazabicyclo[2,2,2]octane.

With Respect to Intermediate (2$^A$)

Next, the intermediate (2$^A$) which is a raw material of the compound (1$^A$) of the present invention is described. In the general formula (2$^A$), a solid line represents a single bond, and a double line represents a double bond. C represents a carbon atom, H represents a hydrogen atom, N represents a nitrogen atom, and O represents an oxygen atom. $R^4$ to $R^{12}$ are the same as $R^4$ to $R^{12}$ defined in the general formula (1$^A$).

The intermediate (2$^A$) can be synthesized by reacting a compound represented by the following general formula (4$^A$)

[Chem. 9]

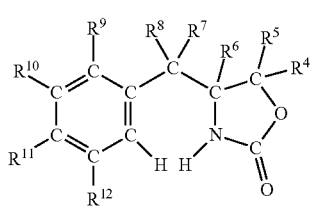

4$^A$ (wherein in the formula (4$^A$), a solid line, a double line, C, H, N, O, and $R^4$ to $R^{12}$ are the same as the solid line, the double line, C, H, N, O, and $R^4$ to $R^{12}$ to defined in the general formula (2$^A$)) and glyoxal trimer dihydrate (5) in the presence of sulfuric acid according to a technique described in publicly known literature (Synthesis, 2014, 2780.) (Eq. 1).

[Chem. 10]

Eq. 1

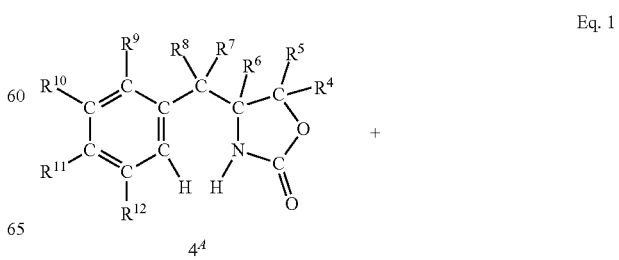

4$^A$

-continued

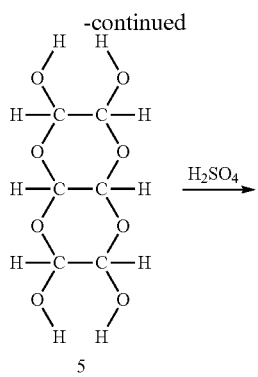

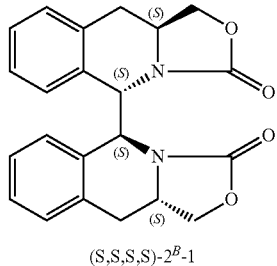

(S,S,S,S)-2$^B$-1

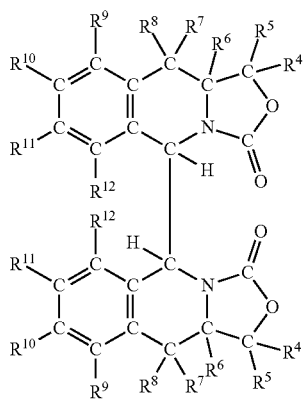

2$^A$

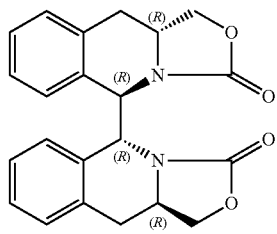

(R,R,R,R)-2$^B$-1

The intermediate (2$^A$) may be an optically active substance. Specific examples of a preferable form of the intermediate (2$^A$) include a compound represented by the following general formula (2$^B$) (hereinafter, referred to as an intermediate (2$^B$))

[Chem. 11]

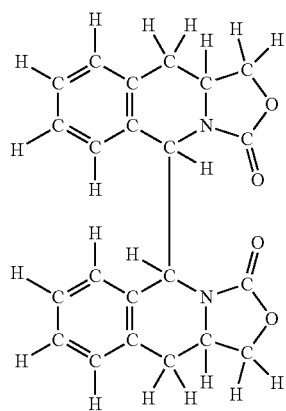

2$^B$ (wherein in the formula (2$^B$), a solid line, a double line, C, H, N, and O are the same as the solid line, the double line, C, H, N, and O defined in the general formula (2$^A$)) in which all of the R$^4$ to R$^{12}$ in the general formula (2$^A$) are hydrogen atoms.

Specific particularly preferable forms of the intermediate (2$^A$) include an intermediate ((S,S,S,S)-2$^B$-1) to an intermediate ((R,R,R,R) 2$^B$-1) shown below.

With Respect to Method for Producing Compound (1$^A$) of Present Invention

Next, a method for producing the compound (1$^A$) of the present invention is described in detail. The compound (1$^A$) of the present invention can be easily obtained by the reaction of the intermediate (2$^A$) with a compound represented by general formula (3) (hereinafter, referred to as a compound (3)) (Eq. 2).

[Chem. 13]

Eq. 2

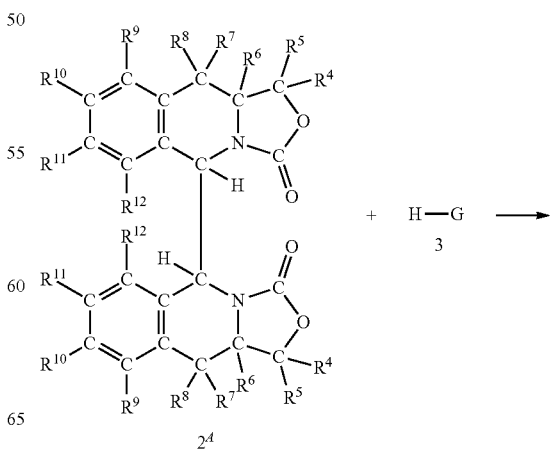

-continued

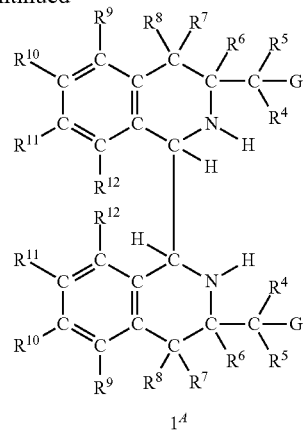

First, the compound (3) is described in detail while referring to specific examples. In the general formula (3), a solid line represents a single bond, and H represents a hydrogen atom. G represents the same group as G defined in the general formula ($1^A$). Specific examples of the compound (3) include a compound represented by the following formula ($3^P$) (hereinafter, referred to as a compound ($3^P$))

[Chem. 14]

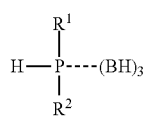

$3^P$ (wherein in the formula ($3^P$), a solid line represents a single bond and a broken line represents a coordinate bond; H represents a hydrogen atom, and P represents a phosphorus atom; $BH^3$ represents boron trihydride; A subscript n represents a coordination number of $BH^3$ to P and indicates an integer value of 0 or 1; $R^1$ and $R^2$ represent the same groups as $R^1$ and $R^2$ defined in the general formula ($1^A$)), namely a secondary phosphine and a boron trihydride complex of a secondary phosphine, and a compound represented by the following general formula ($3^S$) (hereinafter, referred to as a compound ($3^S$))

[Chem. 15]

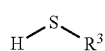

$3^S$ (wherein in the formula ($3^S$), a solid line represents a single bond; H represents a hydrogen atom, and S represents a sulfur atom; $R^3$ represents the same group as $R^3$ defined in the general formula ($1^A$)), namely thiols.

Specific examples of the compound ($3^P$) include secondary phosphines such as dimethyl phosphine ($3^P$-1), diethyl phosphine ($3^P$-2), diisopropyl phosphine ($3^P$-3), di-tert-butyl phosphine ($3^P$-4), dicyclopentyl phosphine ($3^P$-5), dicyclohexylphosphine ($3^P$-6), di-1-adamantylphosphine ($3^P$-7), tert-butylphenylphosphine ($3^P$-8), diphenylphosphine ($3^P$-9), bis(2-methylphenyl)phosphine ($3^P$-10), bis(4-methylphenyl)phosphine ($3^P$-11), bis(3,5-dimethylphenyl) phosphine ($3^P$-12), bis(2,4,6-trimethylphenyl)phosphine ($3^P$-13), bis(2-methoxyphenyl)phosphine ($3^P$-14), bis(4-methoxyphenyl)phosphine ($3^P$-15), bis[4-(trifluoromethyl) phenyl]phosphine ($3^P$-16), bis[3,5-bis(trifluoromethyl)phenyl]phosphine ($3^P$-17), bis(3,5-di-tert-butyl-4-methoxyphenyl)phosphine ($3^P$-18), (11bS)-4,5-dihydro-3H-dinaphtho[2,1-c:1',2'-e]phosphepine ($3^P$-19), and di-2-furylphosphine ($3^P$-20), and boron-trihydride complexes of these secondary phosphines [dimethyl phosphine-borane ($3^P$-1') to di-2-furylphosphine-borane ($3^P$-20')], and preferable specific examples thereof include diphenyl phosphine ($3^P$-9), dicyclohexylphosphine-borane ($3^P$-6'), bis(4-methylphenyl)phosphine-borane ($3^P$-11'), and bis(3,5-dimethylphenyl)phosphine-borane ($3^P$-12') shown by the following structural formulae.

[Chem. 16]

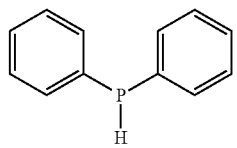

$3^P$-9

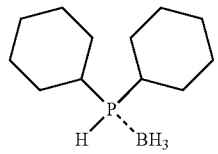

$3^P$-6'

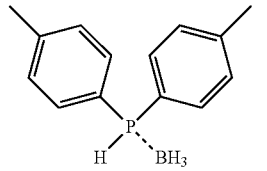

$3^P$-11'

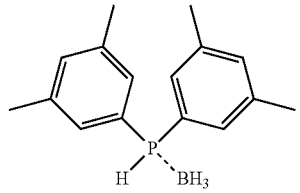

$3^P$-12'

Among the compound ($3^P$), since the secondary phosphine is generally unstable to air and therefore, in order to facilitate the handling, the secondary phosphine may form a salt with a Bronsted acid, specifically, tetrafluoroboric acid. The salt of the secondary phosphine with a Bronsted acid may be used for the reaction with the intermediate ($2^A$) after liberating the secondary phosphine by treating with a base outside the reaction system or may be used for the reaction with the intermediate ($2^A$) while liberating the secondary phosphine by treating with a base in the reaction system.

In the reaction of the intermediate ($2^A$) with compound ($3^P$), as a substitute for compound ($3^P$), a monovalent anion derived from secondary phosphine (i.e. secondary phosphide) or a monovalent anion derived from a boron trihydride complex of secondary phosphine (i.e. boron trihydride complex of secondary phosphide) may be used. These secondary phosphide and boron trihydride complex of secondary phosphide can be easily prepared by subjecting compound ($3^P$) to a reaction with a base. The secondary phosphide can also be prepared by other reactions, and specific examples thereof include a reaction of a secondary phosphine halide with an alkali metal, a reaction of a secondary phosphine dimer with an alkali metal, and a reaction of a tertiary phosphine with an alkali metal.

Specific examples of the compound ($3^S$), namely a thiol, include methanethiol) ($3^S$-1), ethanethiol ($3^S$-2), 1-propanethiol ($3^S$-3), 2-propanethiol ($3^S$-4), 1-butanethiol ($3^S$-5), 2-butanethiol ($3^S$-6), 2-methyl-1-propanethiol ($3^S$-7), 2-methyl-2-propanethiol ($3^S$-8), 1-pentanethiol ($3^S$-9), 3-methyl-1-butanethiol ($3^S$-10), cyclopentanethiel ($3^S$-11), 1-hexanethiol ($3^S$-12), cyclohexanethiol ($3^S$-13), 1-heptanethiol ($3^S$-14), 1-octanethiol ($3^S$-15), 1-nonanediol ($3^S$-16), 1-decanethiol ($3^S$-17), 1-adamantanethiol ($3^S$-18), benzenethiol ($3^S$-19), o-toluenethiol ($3^S$-20), m-toluenethiol ($3^S$-21), p-toluenethiol ($3^S$-22), 2,4-dimethylbenzenethiol ($3^S$-23), 2,5-dimethylbenzenethiol ($3^S$-24), 3,4-dimethylbenzenethiol ($3^S$-25), 3,5-dimethylbenzenethiol ($3^S$-26), 4-isopropylbenzenethiol ($3^S$-27), 4-tert-butylbenzenethiol ($3^S$-28), 2-methoxybenzenethiol ($3^S$-29), 4-methoxybenzenethiol ($3^S$-30), 2,5-dimethoxybertzenethiol ($3^S$-31), 3,4-dimethoxybenzenethiol ($3^S$-32), 2-fluorobenzenethiol ($3^S$-33), 3-fluorobenzenethiol ($3^S$-34), 4-fluorobenzenethiol ($3^S$-35), 2-chlorobenzenethiol ($3^S$-36), 4-chlorobenzenethiol ($3^S$-37), biphenyl-4-thiol ($3^S$-38), 1-naphthalenethiol ($3^S$-39), benzylmercaptan ($3^S$-40), (2,4,6-trimethylphenyl)methanethiol ($3^S$-41), (4-methoxyphenyl)methanethiol ($3^S$-42), (4-fluorophenyl)methanethiol ($3^S$-43), (2-chlorophenyl)methanethiol ($3^S$-44), (4-chlorophenyl)methanethiol ($3^S$-45), triphenylmethanethiol ($3^S$-46), and 9-mercaptofluorene ($3^S$-47), and preferable specific examples thereof include ethanethiol ($3^S$-2) and 2-methyl-2-propanethiol ($3^S$-8) shown by the following structural formulae.

[Chem. 17]

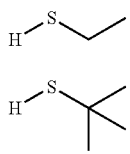

In the reaction of the intermediate ($2^4$) with the compound ($3^S$), namely thiol, as a substitute for thiol generally having a strong malodor, a more easily handled monovalent anion derived from thiol (i.e. thiolate) may also be used. Such a thiolate can be easily prepared by subjecting compound ($3^S$) to a reaction with a base. Specific examples of the thiolate include alkali metal salts of the thiols recited as specific examples above, and preferable specific examples thereof include sodium salt of ethanethiol ($3^S$-2) (sodium ethanethiolate) and sodium salt of 2-methyl-2-propanethiol ($3^S$-8) (sodium 2-methyl-2-propanethiolate).

The reaction of the intermediate ($2^4$) with the compound (3) may be conducted under any of acidic conditions, neutral conditions and basic conditions, but in view of practicality, the reaction is preferably conducted under basic conditions. When the reaction is conducted under basic conditions, specific examples of preferable base include organolithium compounds such as methyllithium, n-butyllithium, sec-butyllithium, tert-butyllithium, and phenyllithium, alkali metal amides such as lithium amide, sodium amide, lithium diisopropyl amide, and lithium hexamethyldisilazide, metal hydrides such as lithium hydride, sodium hydride, potassium hydride, calcium hydride, sodium borohydride, and lithium aluminum hydride. Grignard reagents such as methylmagnesium chloride, tert-butylmagnesium chloride, phenylmagnesium chloride, phenylmagnesium bromide, and methylmagnesium iodide, alkali metal alkoxides such as lithium methoxide, sodium methoxide, potassium methoxide, sodium ethoxide, potassium ethoxide, sodium tert-butoxide, and potassium tert-butoxide, alkali metal hydroxides such as lithium hydroxide, sodium hydroxide, and potassium hydroxide, alkaline earth metal hydroxides such as calcium hydroxide, strontium hydroxide, and barium hydroxide, alkali metal phosphates such as sodium phosphate and potassium phosphate, alkali metal carbonates such as lithium carbonate, sodium carbonate, and potassium carbonate, and alkali metal carboxylates such as sodium acetate and potassium acetate, and preferable specific examples thereof include n-butyllithium. Each of these bases may be used alone, or two or more thereof may be used appropriately in combination.

The amount of the base used is not particularly limited but is appropriately selected from the range of usually from 0.3 to 10 equivalents, preferably from 0.5 to 5 equivalents, more preferably from 0.8 to 3 equivalents, relative to the compound (3). The method for adding the base in this reaction is not particularly limited, but each of the compound (3) and the base may be added separately, a mixture of the compound (3) and the base (and a solvent) may be added, or the secondary phosphide, secondary phosphide-boron trihydride complex, or thiolate, obtained by subjecting the compound (3) to a reaction with the base (in a solvent), may be added. Accordingly, in the case of subjecting the secondary phosphide, secondary phosphide-boron trihydride complex or thiolate as a substitute for the compound (3) to a reaction with the intermediate ($2^4$), the reaction may be conducted without adding the base.

The reaction of the intermediate ($2^4$) with the compound (3) is preferably conducted in the presence of a solvent. Specific examples of the preferable solvent include aliphatic hydrocarbons such as n-pentane, n-hexane, n-heptane, n-octane, n-decane, cyclohexane, and decalin, aromatic hydrocarbons such as benzene, toluene, xylene, mesitylene, p-cymene, and 1,4-diisopropylbenzene, halogenated aromatic hydrocarbons such as chlorobenzene and o-dichlorobenzene, alcohols such as methanol, ethanol, 2-propanol, n-butanol, tert-butanol, 2-methyl-2-butanol, and 2-ethoxyethanol, polyhydric alcohols such as ethylene glycol, propylene glycol, 1,2-propanediol, and glycerol, ethers such as diethyl ether, diisopropyl ether, tert-butyl methyl ether, cyclopentyl methyl ether, 1,2-dimethoxyethane, ethylene glycol diethyl ether, tetrahydrofuran and 1,4-dioxane, amides such as formamide, N,N-dimethylformamide, N,N-dimethylacetamide, and N-methylpyrrolidone, nitriles such as acetonitrile and benzonitrile, sulfoxides such as dimethyl sulfoxide, and water, and preferable specific examples thereof include n-hexane, 2-methyl-2-butanol, and tetrahydrofuran. Each of these solvents may be used alone, or two or more thereof may be used appropriately in combination. The amount of the solvent used is not particularly limited but is appropriately selected from the range of usually from 0.5 to 200 times by volume, preferably from 1 to 100 times by volume, more preferably from 2 to 50 times by volume, relative to the intermediate ($2^A$).

This reaction is preferably performed in an inert gas atmosphere. Examples of the inert gas specifically include argon gas and nitrogen gas. The reaction temperature is appropriately selected from the range of usually from −78° C. to 200° C., preferably from −20° C. to 175° C., more preferably from 0° C. to 150° C. The reaction time varies depending on the base, the solvent, the reaction temperature, and other conditions but is appropriately selected from the range of usually from 1 minute to 24 hours, preferably from 2 minutes to 12 hours, more preferably from 5 minutes to 8 hours.

The compound ($1^B$) that is a preferable form of the compound ($1^A$) of the present invention can be produced by subjecting the intermediate ($2^B$) to a reaction with the compound (3) using the production method described above (Eq. 3).

[Chem. 18]

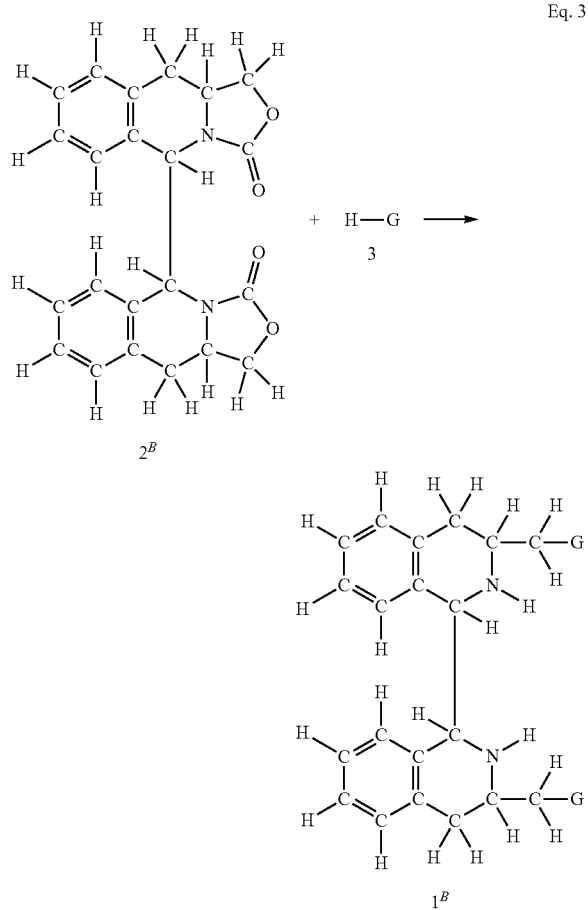

Eq. 3

The thus-obtained compound ($1^A$) of the present invention may be subjected, if desired, to a post-treatment, isolation and purification. The method for the post-treatment includes, for example, concentration, solvent replacement, washing, extraction, filtration, and formation of a salt by the addition of a Brønsted acid, and these methods can be performed independently or in combination. The method for isolation and purification includes, for example, decolorization with an adsorbent, column chromatography, distillation, and crystallization, and these methods can be performed independently or in combination.

With Respect to Transition Metal Complex of Present Invention

The transition metal complex of the present invention is described in detail below. The transition metal complex of the present invention is a transition metal complex having the compound ($1^A$) of the present invention as a ligand. Therefore, the metal species in the transition metal complex of the present invention is not particularly limited as long as the compound ($1^A$) of the present invention can be coordinated thereto, but in view of catalytic activity in an organic synthesis reaction, the metal species is preferably a metal species selected from the group consisting of transition metals of Group 8 to 11, more preferably a metal species selected from transition metals of Group 8, and a particularly preferable metal species include iron and ruthenium.

The transition metal complex of the present invention can be produced by subjecting the compound ($1^A$) of the present invention to a complex formation reaction of a transition metal compound serving as a transition metal source, followed by various chemical conversion reactions such as a ligand exchange reaction and an anion exchange reaction, if necessary. The transition metal compound used in the complex formation reaction is not particularly limited as long as the compound ($1^A$) of the present invention can be coordinated, preferably includes transition metal compounds of Group 8 to 11, that is, an iron compound, a ruthenium compound, an osmium compound, a cobalt compound, a rhodium compound, an iridium compound, a nickel compound, a palladium compound, a platinum compound, a copper compound, a silver compound, and a gold compound, more preferably includes a metal compound of Group 8, that is, an iron compound, a ruthenium compound, and an osmium compound, and particularly preferably includes an iron compound and a ruthenium compound. Hereinafter, the preferable transition metal compounds are described in more detail.

Examples of the iron compound include zerovalent, divalent and trivalent iron compounds and specifically include iron(0) pentacarbonyl, diiron(0) nonacarbonyl, triiron(0) dodecacarbonyl, iron(II) fluoride, iron(II) chloride, iron(II) chloride tetrahydrate, iron(II) bromide, iron(II) iodide, iron (II) sulfate monohydrate, iron(II) sulfate heptahydrate, iron (II) perchlorate hexahydrate, iron(II) trifluoromethanesulfonate, iron(II) tetrafluoroborate hexahydrate, iron(II) acetate, ammonium iron(II) sulfate hexahydrate, iron(II) acetylacetonate, iron(III) fluoride, iron(III) fluoride trihydrate, iron(III) chloride, iron(III) chloride hexahydrate, iron (III) bromide, iron(III) sulfate hydrate, iron(III) nitrate nonahydrate, iron(III) perchlorate hydrate, iron(III) trifluoromethanesulfonate, iron(III) phosphate hydrate, iron (III) acetylacetonate, and iron(III) trifluoroacetylacetonate, and preferable specific examples thereof include iron(II) tetrafluoroborate hexahydrate.

Examples of the ruthenium compound include zerovalent, divalent and trivalent ruthenium compounds, specific examples thereof include triruthenium(0) dodecacarbonyl, dichloro(benzene)ruthenium(II) dimer, dichloro(p-cymene) ruthenium(II) dimer, dichloro(mesitylene)ruthenium(II) dimer, dichloro(hexamethylbenzene)ruthenium(II) dimer, diiodo(p-cymene)ruthenium(II) dimer, dipivalato(p-cymene)ruthenium(II), bis(π-methallyl)(1,5-cyclooctadiene) ruthenium(II), dichloro(1,5-cyclooctadiene)ruthenium(II)

polymer, dichloro(norbornadiene)ruthenium(II) polymer, dichloro tris(triphenylphosphine)ruthenium(II), chlorohydridotris(triphenylphosphine)ruthenium(II) toluene adduct, dihydridotetrakis(triphenylphosphine)ruthenium(II), carbonylchiorohydridotris(triphenylphosphine)ruthenium(II), carbonyldihydridotris(triphenylphosphine)ruthenium(II), dichlorotetrakis(dimethylsulfoxide)ruthenium(II), ruthenium(III) chloride, ruthenium(III) chloride hydrate, ruthenium (III) ruthenium(III) iodide hydrate, hexammineruthertium(III) trichloride, and ruthenium(III) acetylacetonate, and preferable specific examples thereof include dichloro(p-cymene)ruthenium(II) dimer and bis(π-methallyl)(1,5-cyclooctadiene)ruthenium(II).

Examples of the osmium compound includes divalent and trivalent osmium compounds and specifically include dichloro(p-cymene)osmium(II) dimer, carhonylchlorohydridotris(triphenylarsine)osmium(II), osmium(III) chloride, and osmium(III) chloride trihydrate.

Examples of the cobalt compound include divalent and trivalent cobalt compounds, specific examples thereof include cobalt(II) fluoride, cobalt(II) fluoride tetrahydrate, cobalt(II) chloride, cobalt(II) chloride dihydrate, cobalt(II) chloride hexahydrate, cobalt(II) bromide, cobalt(II) bromide dihydrate, cobalt(II) iodide, cobalt(II) sulfate monohydrate, cobalt(II) sulfate heptahydrate, cobalt(II) nitrate hexahydrate, cobalt(II) perchlorate hexahydrate, cobalt(II) tetrafluoroborate hexahydrate, cobalt(II) acetate, cobalt(II) acetate tetrahydrate, cobalt(II) cyanide dihydrate, cobalt(II) acetylacetonate, cobalt(II) acetylacetonate hydrate, cobalt(II) hexafluoroacetylacetonate hydrate, cobalt(III) fluoride, cobalt(III) acetylacetonate, and hexaamminecobalt(III) trichloride.

Examples of the rhodium compound include monovalent, divalent, and trivalent rhodium compounds, specifically chloro(1,5-hexadiene)rhodium(I) dimer, chloro(1,5-cyclooctadiene)rhodium(I) dimer, chlorobis(cyclooctene)rhodium(I) dimer, bis(1,5-cyclooctadiene)rhodium(I) trifluoromethanesulfonate, bis(1,5-cyclooctadiene)rhodium(I) hexafluoroantimonate, bis(1,5-cyclooctadiene)rhodium(I) tetrafluoroborate, bis(norbornmadiene)rhodium(I) trifluoromethanesulfonate, (acetylacetonato)bis(ethylene)rhodium(I), (acetylacetonato)(1,5-cyclooctadiene)rhodium(I), (acetylacetonato)(norbornadiene)rhodium(I), bis(acetonitrile)(1,5-cyclooctadiene)-rhodium(I) tetrafluoroborate, bis (1,5-cyclooctadiene)rhodium(I) tetrakis[bis(3,5-trifluoromethyl)phenyl]borate, tetrakis(triphenylphosphine)rhodium(I) hydride, (acetylacetonato)dicarbonylrhodium(I), rhodium(III)chloride, rhodium(III) chloride trihydrate, rhodium(III) nitrate hydrate, tetrakis(μ-trifluoroacetato)dirhodium(II), tetrakis(μ-acetato)dirhodium(II), tetrakis(μ-acetato)dirhodium(II) dihydrate, tetrakis(μ-trimethylacetato)dirhodium(II), tetrakis(μ-octanoato)dirhodium(II), tetrakis(triphenylacetato)dirhodium II), and rhodium(III) acetylacetonate.

Examples of the iridium compound include monovalent and trivalent iridium compounds and specifically include chloro(1,5-cyclooctadiene)iridium(I) dimer, (1,5-cyclooctadiene)(methoxy)iridium(I) dimer, bis(cyclooctadiene)iridium(I) tetrakis[3,5-bis(trifluoromethyl)phenyl]borate, bis(1,5-cyclooctadiene)iridium(I) tetrafluoroborate, (1,5-cyclooctadiene)(hexafluoroacetylacetonato)iridium(I), (acetylacetonato)(1,5-cyclooctadiene)iridium(I), (acetylacetonato)dicarbonyliridium(I), iridium(III) chloride, iridium (III) chloride hydrate, and iridium(III) acetylacetonate.

Examples of the nickel compound include zerovalent and divalent nickel compounds, specifically bis(1,5-cyclooctadiene)nickel(0), tetrakis(triphenylphosphine)nickel(0), dichlorobis(triphenylphosphine)nickel(II), nickel(II) fluoride, nickel(II) chloride, nickel(II) chloride monohydrate, nickel(II) chloride hexahydrate, nickel(II) bromide, nickel (II) bromide trihydrate, nickel(II) iodide, nickel(II) trifluoromethanesulfonate, nickel(II) sulfate, nickel(II) sulfate hexahydrate, nickel(II) sulfate heptahydrate, nickel(II) nitrate hexahydrate, nickel(II) perchlorate hexahydrate, nickel(II) oxalate dihydrate, nickel(II) acetate tetrahydrate, nickel(II) acetylacetonate, and nickel(II) hexafluoroacetylacetonate hydrate.

Examples of the palladium compound include zerovalent and divalent palladium compounds, specifically bis(dibenzylideneacetone)palladium(0), tris(dibenzylideneacetone)dipalladium(0), tetrakis(triphenylphosphine)palladium(0), bis(acetonitrile)dichloropalladium(II), bis(acetonitrile)dibromopalladium(II), bis(benzonitrile)dichloropalladium(II), bis(benzonitrile)dibromopalladium(II), dichloro(1,5-cyclooctadiene)palladium(II), bis(triphenylphosphine)diehloropalladium(II), (π-allyl)palladium(II) chloride dimer, (π-methallyl)palladium(II) chloride dimer, (π-cinnamyl)palladium(II) chloride dimer, palladium(II) chloride, palladium (II) bromide, palladium(II) iodide, palladium(II) sulfate, palladium(II) nitrate dihydrate, palladium(II) trifluoroacetate, palladium(II) acetate, palladium(II) propionate, palladium(II) pivalate, palladium(II) cyanide, palladium(II) acetylacetonate, palladium(ii) hexafluoroacetylacetonate, tetrakis(acetonitrile)palladium(II) tetrafluoroborate, sodium tetrachloropalladate(II), and potassium tetrachloropalladate(II).

Examples of the platinum compound include divalent and tetravalent platinum compounds and specifically include platinum(II) chloride, platinum(II) bromide, platinum(II) iodide, platinum(II) cyanide, platinum(II) acetylacetonate, potassium tetrachloroplatinate(II), dichloro(1,5-cyclooctadiene)platinum(II), cis-bis(acetonitrile)dichloroplatinum(II), trans-bis(acetonitrile)dichloroplatinum(II), cis-bis(benzonitrile)dichloroplatinum(II), platinum(IV) chloride, and potassium hexachoroplatinate(IV).

Examples of the copper compound include monovalent and divalent copper compounds and specifically include copper(I) oxide, copper(I) chloride, copper(I) bromide, copper(I) iodide, copper(I) trifluoromethanesulfonate benzene complex, copper(I) acetate, copper(I) cyanide, tetrakis(acetonitrile)copper (I) tetrafluoroborate, tetrakis(acetonitrile) copper(I) hexafluorophosphate, copper(II) oxide, copper(II) fluoride, copper(II) fluoride dihydrate, copper(II) chloride, copper(II) chloride dihydrate, copper(II) bromide, copper (II) trifluoromethanesulfonate, copper(II) sulfate, copper(II) sulfate pentahydrate, copper(II) nitrate trihydrate, copper(II) perchlorate hexahydrate, copper(II) tetrafluoroborate hexahydrate, copper(II) trifluoroacetate, copper(II) acetate, copper(II) acetate monohydrate, copper(II) acetylacetonate, and copper(II) hexafluoroacetylacetonate hydrate.

Examples of the silver compound include monovalent and divalent silver compounds and specifically include silver(I) oxide, silver(I) fluoride, silver(I) chloride, silver(I) bromide, silver(I) trifluoromethanesulfonate, silver(I) methanesulfonate, silver(I) p-toluenesulfontate, silver(I) sulfate, silver(I) nitrate, silver(I) perchlorate, silver(I) perchlorate monohydrate, silver(I) tetrafluoroborate, silver(I) hexafluorophosphate, silver(I) trifluoroacetate, silver(I) acetate, silver(I) benzoate, silver(I) carbonate, silver(I) nitrite, silver(I) cyanate, silver(I) acetylacetonate, silver(II) fluoride, and silver(II) picolinate.

Examples of the gold compound include monovalent and trivalent gold compounds and specifically include gold(I) chloride, gold(I) iodide, gold(I) cyanide, gold(III) chloride, gold(III) chloride dihydrate, gold(III) bromide, chloroauric acid(III) tetrahydrate, and potassium chloroaurate(III).

A ligand source and an anion source used in chemical conversion reactions such as a ligand exchange reaction and an anion exchange reaction are not particularly limited as long as they do not inhibit coordination action of the compound ($1^A$) of the present invention, and preferable specific examples thereof include 1,1,3,3-tetramethylbutylisocyanide, 1-isocyanoadamantane, tetrabutylammonium bromide, and sodium borohydride.

In the production of the transition metal complex of the present invention, a solvent is preferably allowed to coexist. The solvent is not particularly limited as long as it does not inhibit the coordination action of the compound ($1^A$) of the present invention, and preferable specific examples thereof include toluene, chloroform, acetone, acetonitrile, butyronitrile, ethanol, and 1-butanol. Each of these solvents may be used alone, or two or more thereof may be used appropriately in combination. These solvents may be incorporated into the transition metal complex of the present invention as a solvent of crystallization or a ligand. In production of the transition metal complex of the present invention, an acid and a base may be allowed to coexist, if desired, and the production may be performed in an inert gas atmosphere such as nitrogen and argon.

The thus-obtained transition metal complex of the present invention may be subjected, if desired, to a post-treatment, isolation and purification. Examples of the method for the post-treatment include concentration, solvent replacement, washing, extraction, and filtration, and these post-treatments can be performed independently or in combination. Examples of the method for isolation and purification include decolorization with an adsorbent, column chromatography, crystallization, and sublimation, and these methods can be performed independently or in combination.

In the case of using the transition metal complex of the present invention as a catalyst in an organic synthesis reaction, the transition metal complex of the present invention may be used without isolating it from the reaction solution or may be used after performing, if desired, the above-described post-treatment, isolation and purification, and each may be used alone or two or more may be appropriately used in combination. Furthermore, the organic synthesis reaction using the complex as a catalyst may be performed while preparing the transition metal complex of the present invention by adding the compound ($1^A$) of the present invention and a transition metal compound, and if desired, a ligand source and/or an anion source to the inside of the organic synthesis reaction system.

The compound ($1^A$) of the present invention acts mainly as a chiral tetradentate ligand but may act as a bidentate ligand or a tridentate ligand depending on the structure of the transition metal compound reacted and may also act as a crosslinking ligand between the same or different metals. Accordingly, the transition metal complex of the present invention may be not only a mononuclear complex (a complex having only one metal atom) but also a polynuclear complex (a complex having two or more metal atoms, irrespective of the same or different), but in view of catalytic activity in view of organic synthesis, it is more preferable to be a mononuclear complex.

Specific preferable forms of the transition metal complex of the present invention include $\{Fe[(S,S,S,S)-1^B-1](CH_3CN)_2\}(BF_4)_2$ to $RuH(BH_4[(R,R,R,R)-1^B-1]$ shown below. The coordination form of these transition metal complexes may be any of trans, cis-α, or

[Chem. 19]

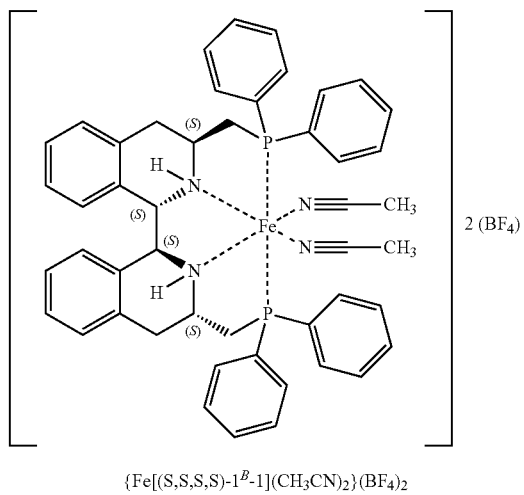

$\{Fe[(S,S,S,S)-1^B-1](CH_3CN)_2\}(BF_4)_2$

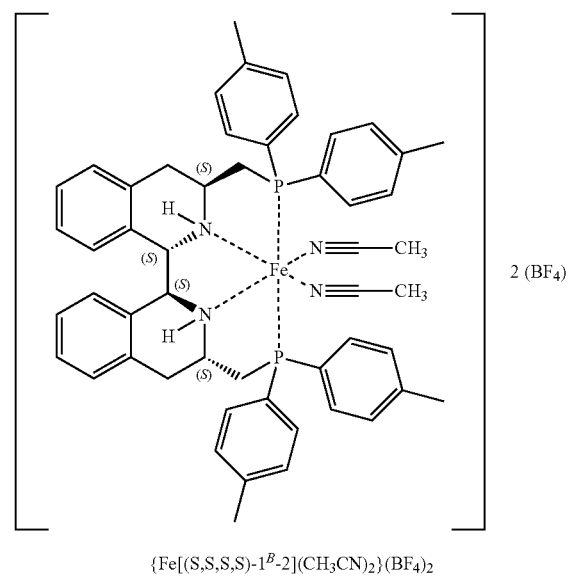

$\{Fe[(S,S,S,S)-1^B-2](CH_3CN)_2\}(BF_4)_2$

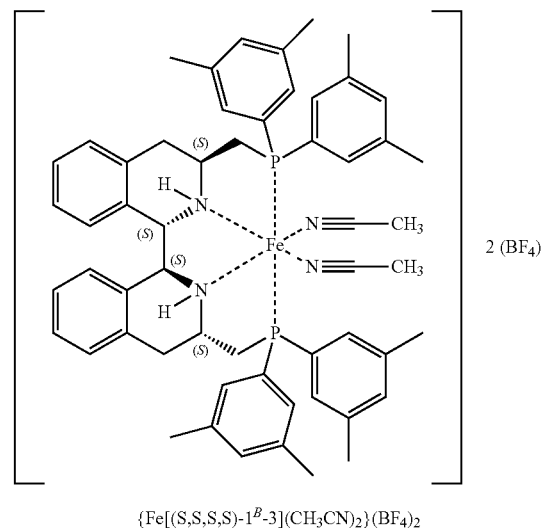

$\{Fe[(S,S,S,S)-1^B-3](CH_3CN)_2\}(BF_4)_2$

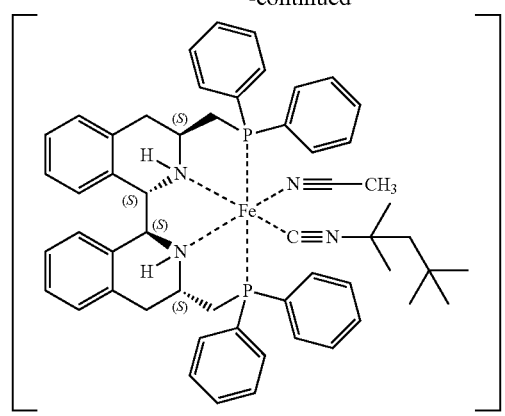
{Fe[(S,S,S,S)-1^B-1](t-OcNC)(CH₃CN)}(BF₄)₂
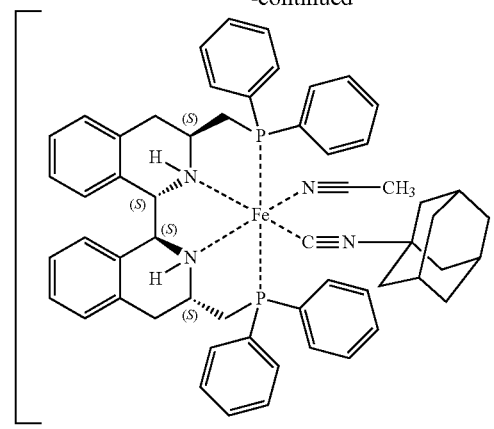
{Fe[(S,S,S,S)-1^B-1](AdNC)(CH₃CN)}Br₂
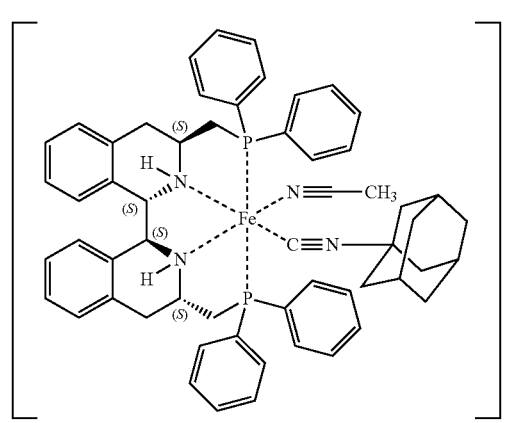
{Fe[(S,S,S,S)-1^B-1](AdNC)(CH₃CN)}(BF₄)₂
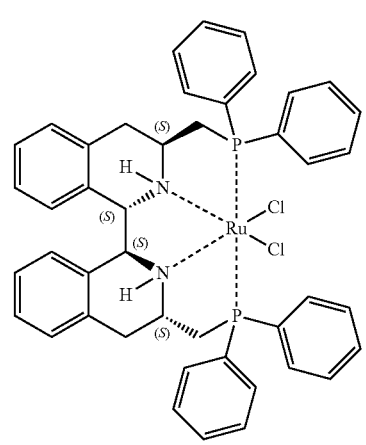
RuCl₂[(S,S,S,S)-1^B-1]
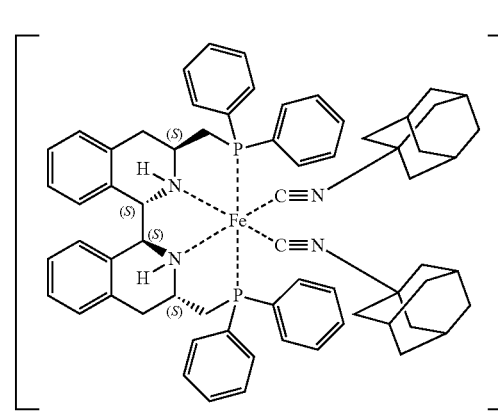
{Fe[(S,S,S,S)-1^B-1](AdNC)₂}(BF₄)₂
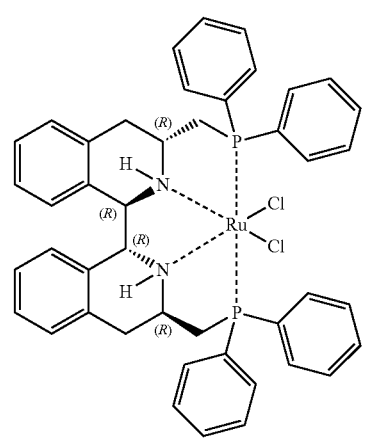
RuCl₂[(R,R,R,R)-1^B-1]

-continued

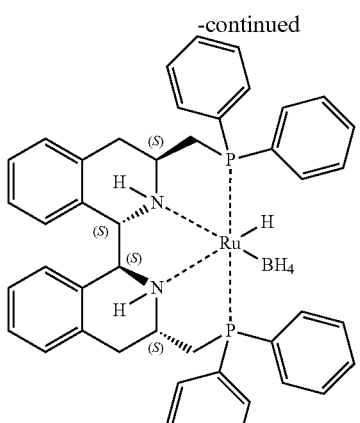

RuH(BH₄)[(S,S,S,S)-1$^B$-1]

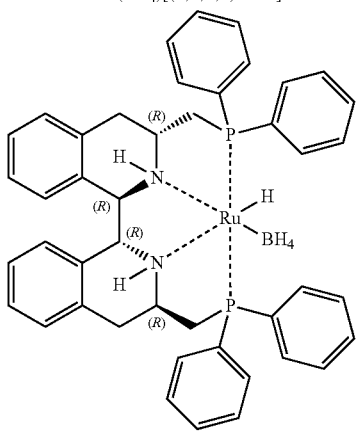

RuH(BH₄)[(R,R,R,R)-1$^B$-1]

The compound (1$^A$) of the present invention is useful as a ligand in a variety of catalytic organic synthesis reactions, and the transition metal complex of the present invention is useful as a catalyst in a variety of organic synthesis reactions. The organic synthesis reaction is not particularly limited but specifically includes an oxidation reaction, a reduction reaction, a hydrogenation reaction, a dehydrogenation reaction, a transfer hydrogenation reaction, an addition reaction, a conjugate addition reaction, a pericyclic reaction, a functional group conversion reaction, an isomerization reaction, a rearrangement reaction, a polymerization reaction, a bond formation reaction, and a bond cleavage reaction, and preferably includes a hydrogenation reaction and a transfer hydrogenation reaction, and preferable specific examples thereof include a hydrogenation reaction of ketones and esters and a transfer hydrogenation reaction of ketones.

EXAMPLES

The compound of the present invention, the transition metal complex of the present invention, and the catalytic reaction using the transition metal complex of the present invention are described in detail below by referring to Examples, but the present invention is not limited by these Examples in any way. In Examples, the following apparatuses and conditions were employed for the measurements of physical properties.

1) Proton nuclear magnetic resonance spectroscopy ($^1$H NMR): Model 400MR DD2 apparatus (resonance frequency: 400 MHz, manufactured by Agilent Technology Inc.)
2) Carbon 13 nuclear magnetic resonance spectroscopy ($^{13}$C NMR): Model 400MR DD2 apparatus (resonance frequency: 100 MHz, manufactured by Agilent Technology Inc.)
3) Phosphorus 31 nuclear magnetic resonance spectroscopy ($^{31}$P NMR): Model 400MR DD2 apparatus (resonance frequency: 161 MHz, manufactured by Agilent. Technology Inc.)
4) Gas chromatography (GC): Model GC-4000P1 US apparatus (manufactured by GL Sciences Inc.)

[Measurement Condition 1] Column: CP-Chirasil-DEX CB (manufactured by Agilent Technology Inc.), injector temperature: 250° C., detector temperature: 250° C., measurement temperature: 120° C., analysis time: 20 minutes.

[Measurement Condition 2] Column: InertCap 1 (manufactured by GL Sciences Inc.), injector temperature: 250° C., detector temperature: 250° C., initial temperature: 50° C., temperature rate: 10° C./min, final temperature: 250° C., holding time at final temperature: 10 minutes.

Examples 1 and 2 relate to production of the intermediate (2$^A$), Examples 3 to 9 relate to production of the compound (1$^A$) of the present invention, Examples 10 to 20 relate to production of the transition metal complex of the present invention, Examples 21 to 24 relate to an organic synthesis reaction using the transition metal complex of the present invention as a catalyst, and Example 25 relates to an organic synthesis reaction using the compound (1$^A$) of the present invention as a ligand. Unless otherwise noted, the substrate and solvent were charged under nitrogen stream, the reaction was carried out under a nitrogen atmosphere, and the post-treatment of the reaction solution and the isolation and purification of the crude product were carried out in air.

[Example 1] Synthesis of Intermediate ((S,S,S,S)-2$^B$-1) (Eq. 4)

[Chem. 20]

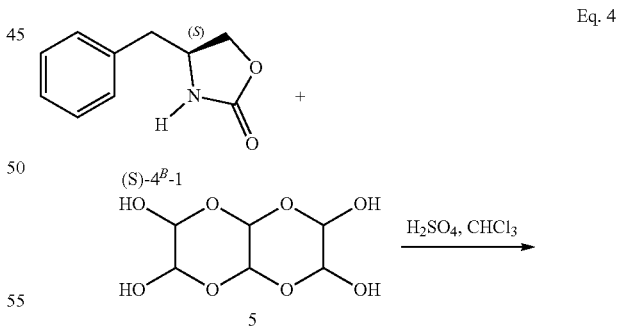

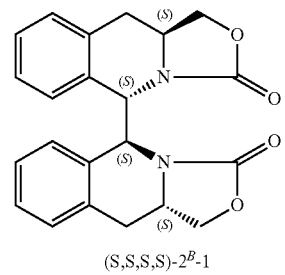

(S,S,S,S)-2$^B$-1

Eq. 4

The target intermediate ((S,S,S,S)-$2^B$-1) was synthesized according to a technique described in the publicly known literature (Synthesis, 2014, 2780.). A 500 mL four-necked round-bottom flask equipped with a magnetic stirring bar, thermometer, dropping funnel, condenser, and a three-way stopcock was evacuated and filled with nitrogen gas. Glyoxal trimer dihydrate (5) (purity: 95%, 5.2 g, 23.5 mmol, 1.0 equivalent), (S)-4-benzyl-2-oxazolidinone ((S)-$4^B$-1) (25.0 g, 141.1 mmol, 6.0 equivalents), and dehydrated chloroform (CHCl$_3$) (250 mL) were charged into the flask successively, and obtained suspension was heated by means of an oil bath while stirring with a magnetic stirrer and thereby refluxed. Subsequently, sulfuric acid (H$_2$SO$_4$) (purity: 96.4%, 28.7 g, 282.2 mmol, 12.0 equivalents) was charged into the dropping funnel and added dropwise into the flask over 20 minutes under reflux while stirring, and then the reaction mixture was stirred for 6 hours under reflux. After the reaction mixture was cooled to room temperature, water (200 mL) was charged into the mixture, followed by stirring with a magnetic stirrer, and suction filtration was performed using diatomaceous earth. The obtained filtrate was left to stand and the aqueous layer was separated. The aqueous layer was extracted with CHCl$_3$ (100 mL), and then the organic layers were combined and washed with water (50 mL). Silica gel (5 g) was added to the organic layer and the mixture was stirred for 10 minutes at room temperature and then filtered by suction using diatomaceous earth, and the residue was washed with chloroform (100 mL). Silica gel (5 g) was added to the obtained filtrate and the mixture was stirred for 10 minutes at room temperature and then filtered by suction using diatomaceous earth, and the residue was washed with chloroform (100 mL). This series of operations (silica gel charging, stirring, suction filtration, and washing) was repeated once more, and the obtained filtrate was concentrated under reduced pressure to about 70 g. After ethyl acetate (150 mL) was added to the concentrate mixture suction filtration was performed and the obtained powder was washed with ethyl acetate (50 mL) and then dried, in vacuo to give 18.2 g of the target intermediate ((S,S,S,S)-$2^B$-1) as a cream-colored powder. Yield: 18.2 g, isolated yield: 68.9%.

$^1$H NMR (400 MHz, CD$_2$Cl$_2$): δ=7.26 (dt, J=1.2, 7.6 Hz, 2H), 7.20 (dd, J=0.8, 7.6 Hz, 2H), 7.08 (dt, J=0.8, 7.6 Hz, 2H), 6.68 (d, J=7.6 Hz, 2H), 5.14 (s, 2H), 4.55 (t, J=8.4 Hz, 2H), 4.51-4.41 (m, 2H), 4.09 (dd, J=8.4 Hz, 2H), 3.14 (dd, J=5.6, 16.4 Hz, 2H), 2.91 (dd, J=10.4, 16.4 Hz, 2H).

$^{13}$C NMR (100 MHz, CD$_2$Cl$_2$): δ=157.78, 133.48, 131.68, 130.39, 129.93, 128.42, 126.07, 69.61, 57.13, 49.19, 33.76.

[Example 2] Synthesis of Intermediate ((R,R,R,R)-$2^B$-1) (Eq. 5)

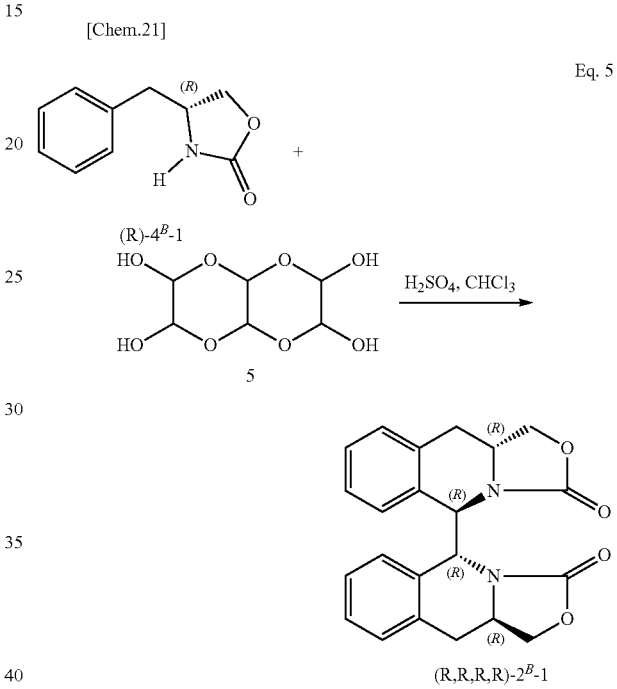

The target intermediate ((R,R,R,R)-$2^B$-1) was synthesized in the same manner as in Example 1, except that (R)-4-benzyl-2-oxazolidinone ((R)-$4^B$-1) was used instead of (S)-4-benzyl-2-oxazolidinone ((S)-$4^B$-1), Yield: 18.8 g, isolated yield: 70.8%. The results of NMR measurement were the same as in Example 1.

[Example 3] Synthesis of Compound ((S,S,S,S)-$1^B$-1) (Eq. 6)

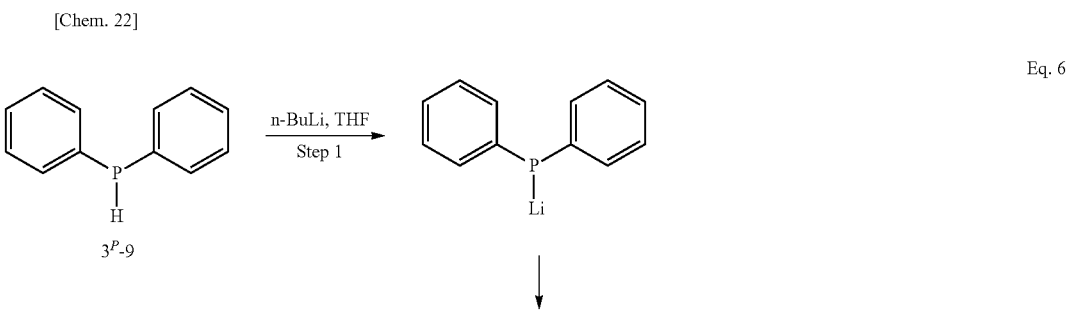

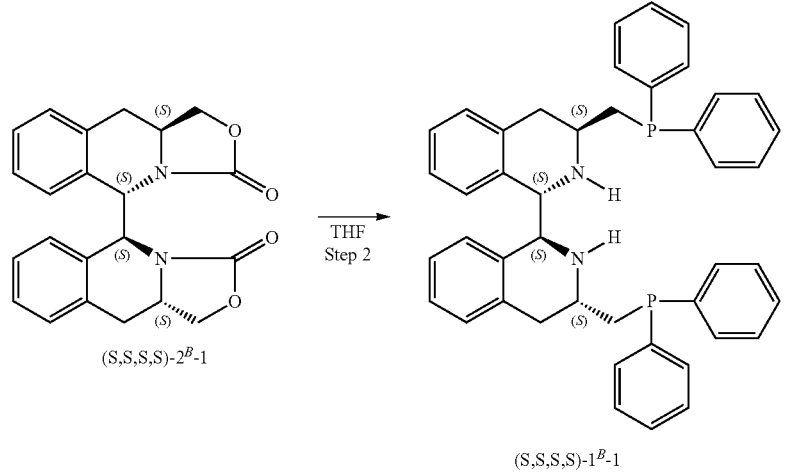

(S,S,S,S)-2^B-1 → (S,S,S,S)-1^B-1

THF
Step 2

First step: A 100 mL four-necked round-bottom flask equipped with a magnetic stirring bar, dropping funnel, thermometer, and a three-way stopcock was evacuated and filled with nitrogen gas. Diphenylphosphine (3^P-9) (purity: 97%, 10.0 g, 52.1 mmol, 2.2 equivalents) and dehydrated tetrahydrofuran (THF) (52 mL) were charged into the flask successively, and the obtained solution was cooled to 5° C. by means of an ice-water bath while stirring with a magnetic stirrer. Subsequently, an n-hexane solution of n-butyllithium (n-BuLi) (concentration: 2.65 mol/L, 19.7 mL, 52.1 mmol, 2.2 equivalents) was charged into the droppinp, funnel, and added dropwise into the reaction solution over 30 minutes at a rate keeping the inner temperature at 10° C. or less while stirring the solution. Thereafter, the ice-water bath was removed, and the obtained solution was stirred for 20 minutes at room temperature to give a THF/n-hexane solution of lithium dipbenylphosphide (52.1 mmol, 2.2 equivalents) as a reddish-orange liquid.

Second step: A 500 mL four-necked round-bottom flask equipped with a magnetic stirring bar, condenser, dropping funnel, thermometer, and a three-way stopcock was evacuated and filled with nitrogen gas. The intermediate ((S,S,S,S)-2^B-1) obtained in Example 1 (8.9 g, 23.7 mmol, 1.0 equivalent) and dehydrated THF (47 mL) were charged into the flask successively, and the obtained suspension was heated by means of an oil bath while stirring with a magnetic stirrer thereby refluxed. Subsequently, the THF/n-hexane solution of lithium diphenylphosphide (52.1 mmol, 2.2 equivalents) prepared in the first step was charged into the dropping funnel, and added dropwise into the suspension over one hour under reflux while stirring, and then the reaction mixture was stirred for one hour under reflux. After about 95 of the reaction solvent was recovered from the reaction mixture under reduced pressure, toluene (200 mL), water (100 mL), and concentrated hydrochloric acid (4 mL) were charged into the mixture successively, while stirring the obtained concentrated mixture with a magnetic stirrer, and then the mixture was filtered by suction using diatomaceous earth. The obtained filtrate was left to stand and the aqueous layer was separated. The aqueous layer was extracted with toluene (50 mL), and then the organic layers were combined and washed with water (50 mL). The organic layer was concentrated under reduced pressure, and the residue was purified by silica gel column chromatography (eluent: toluene/ethyl acetate/triethylamine=100/10/1) to give a target compound ((S,S,S,S)-1^B-1) as an orange viscous liquid. Yield: 21.0 g, purity: 70.0% (an impurity was toluene), net weight: 14.7 g, isolated yield: 93.9%. Since the compound had extremely high viscosity, the compound was diluted with toluene to prepare the solution thereof (concentration: about 25%) to facilitate handling, and then stored under nitrogen atmosphere.

$^1$H NMR (400 MHz, CD$_2$Cl$_2$): δ=7.42-7.22 (m, 20H), 7.19-7.11 (m, 2H), 7.10-7.02 (m, 4H), 6.78 (d, J=7.6 Hz, 2H), 4.40 (s, 2H), 3.41-3.31 (m, 2H), 2.94 (dd, J=4.8, 16.0 Hz, 2H), 2.60 (dd, J=6.8, 16.0 Hz, 2H), 2.19 (d, J=7.2 Hz, 4H), 1.77 (br s, 2H).

$^{31}$P NMR. (161 MHz, CD$_2$Cl$_2$): δ=23.75 (s, 2 P).

[Example 4] Synthesis of Compound ((R,R,R,R)-1^B-1) (Eq. 7)

[Chem. 23]

Eq. 7

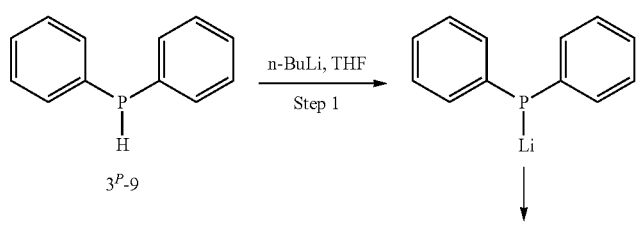

3^P-9 → (Li)

n-BuLi, THF
Step 1

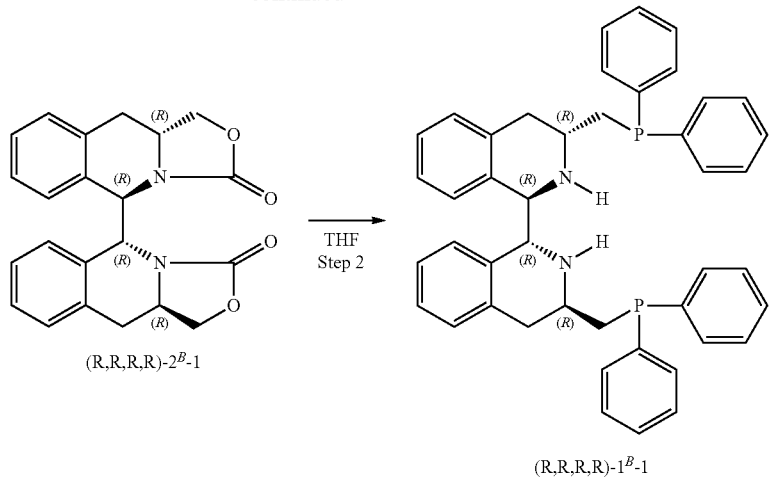

(R,R,R,R)-2^B-1

(R,R,R,R)-1^B-1

A target compound ((R,R,R,R)-1^B-1) was synthesized in the same manner as in Example 3, except that the intermediate ((R,R,R,R)-2^B-1) obtained in Example 2 was used instead of the intermediate ((S,S,S,S)-2^B-1). Yield: 17.9 g, purity: 72.2% (an impurity was toluene), net weight: 12.9 g, isolated yield: 82.6%. Since the compound had extremely high viscosity, the compound was diluted with toluene to prepare the solution thereof (concentration: about 25%) to facilitate handling, and then stored under nitrogen atmosphere. The results of NMR measurement were the same as in Example 3.

[Example 5] Synthesis of Compound ((S,S,S,S)-1^B-2) (Eq. 8)

[Chem. 24]

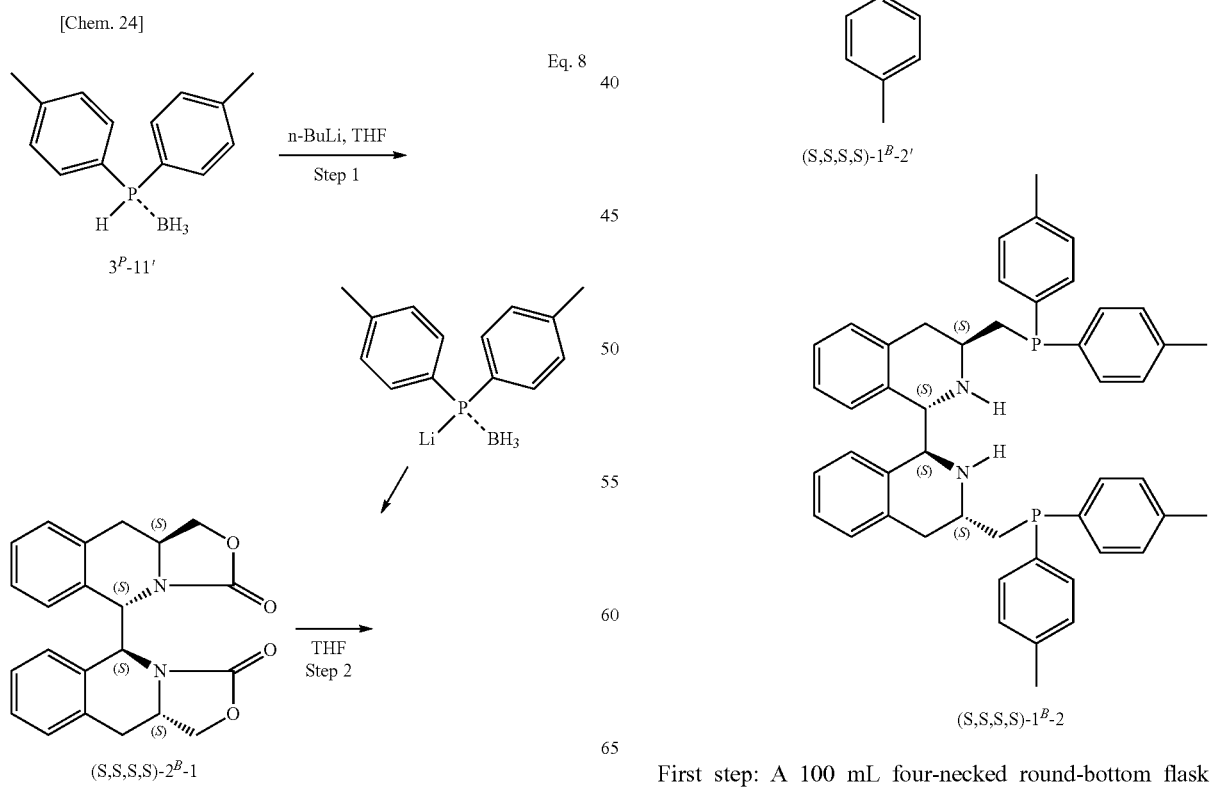

First step: A 100 mL four-necked round-bottom flask equipped with a magnetic stirring bar, dropping funnel, thermometer, and a three-way stopcock was evacuated and filled with nitrogen gas. Bis(4-methylphenyl)phosphine-borane ($3^P$-11') (6.0 g, 26.3 mmol, 2.1 equivalents) and dehydrated THF (53 mL) were charged into the flask successively, and the obtained solution was cooled to 5° C. by means of an ice-water bath while stirring with a magnetic stirrer. Subsequently, an n-hexane solution of n-BuLi (concentration: 2.65 mol/L, 9.9 mL, 26.3 mmol, 2.1 equivalents) was charged into the dropping funnel, and added dropwise into the solution over 30 minutes at a rate keeping the inner temperature at 10° C. or less while stirring the solution. Thereafter, the ice-water bath was removed, and the obtained solution was stirred for one hour at room temperature to give a THF/n-hexane solution of lithium bis(4-methylphenyl)phosphide-borane (26.3 mmol, 2.1 equivalents) as a dark-brown liquid.

Second step: A 500 mL four-necked round-bottom flask equipped with a magnetic stirring bar, condenser, dropping funnel, thermometer, and a three-way stopcock was evacuated and filled with nitrogen gas. The intermediate ((S,S,S,S)-$2^B$-1) obtained in Example 1 (4.7 g, 12.5 mmol, 1.0 equivalent) and dehydrated THF (25 mL) were charged into the flask successively, and the obtained suspension was heated by means of an oil bath while stirring with a magnetic stirrer thereby reflux. Subsequently, the n-hexane/THF solution of lithium bis(4-methylphonyl)phosphide-borane (26.3 mmol, 2.1 equivalents) prepared in the first step was charged into the dropping funnel, and added dropwise into the suspension over 30 minutes under reflux while stirring, and then the obtained reaction mixture was for one hour under reflux. The reaction mixture was concentrated under reduced pressure, toluene (200 mL) and water (200 mL) were added thereinto successively, followed by stirring, and after leaving to stand, the aqueous layer was separated. The obtained organic layer was washed with water (50 mL) and then concentrated under reduced pressure to give a crude product (12.5 mmol, 1.0 equivalent) of the compound ((S,S,S,S)-$1^B$-2').

$^{31}$P NMR (161 MHz, CDCl$_3$): δ=11.02 (br s, 2 P).

Third step: A 200 mL four-necked round-bottom flask equipped with a magnetic stirring bar, condenser, thermometer, and a three-way stopcock was evacuated and filled with nitrogen gas. The crude product of the compound ((S,S,S,S)-$1^B$-2') (12.5 mmol, 1.0 equivalent) prepared in the second step, toluene (100 mL) and 1,4-diazabicyclo[2,2,2]octane (DABCO) (4.2 g, 37.5 mmol, 3.0 equivalents) were charged into the flask successively, the obtained cream-colored slurry was heated by means of an oil bath while stirring with a magnetic stirrer, and the mixture was stirred for one hour under reflux. The reaction mixture was cooled to room temperature, washed with water (50 mL), and then concentrated under reduced pressure. The obtained residue was purified by silica gel column chromatography (eluent: toluene/ethyl acetate/triethylamine=100/10/1) to give a target compound ((S,S,S,S)-$1^B$-2) as an orange viscous liquid. Yield: 8.9 g, purity: 89.0% (an impurity was toluene), net weight: 7.9 g, isolated yield: 88.4%. Since the compound had extremely high viscosity, the compound was diluted with toluene to prepare the solution thereof (concentration: about 25%) to facilitate handling, and then stored under nitrogen atmosphere.

$^1$H NMR (400 MHz, CD$_2$Cl$_2$): δ=7.31-7.01 (m, 22H), 6.70 (d, J=7.6 Hz, 2H), 4.39 (s, 2H), 3.50-3.25 (m, 2H), 3.01-2.85 (m, 2H), 2.80-2.60 (m, 2H), 2.32 (s, 6H), 2.30 (s, 6H), 2.22 (br m, 4H), 1.65 (br s, 2H).

$^{31}$P NMR (161 MHz, CD$_2$Cl$_2$): δ=−26.49 (s, 2 P).

[Example 6] Synthesis of Compound ((S,S,S,S)-$1^B$-3) (Eq. 9)

[Chem. 25]

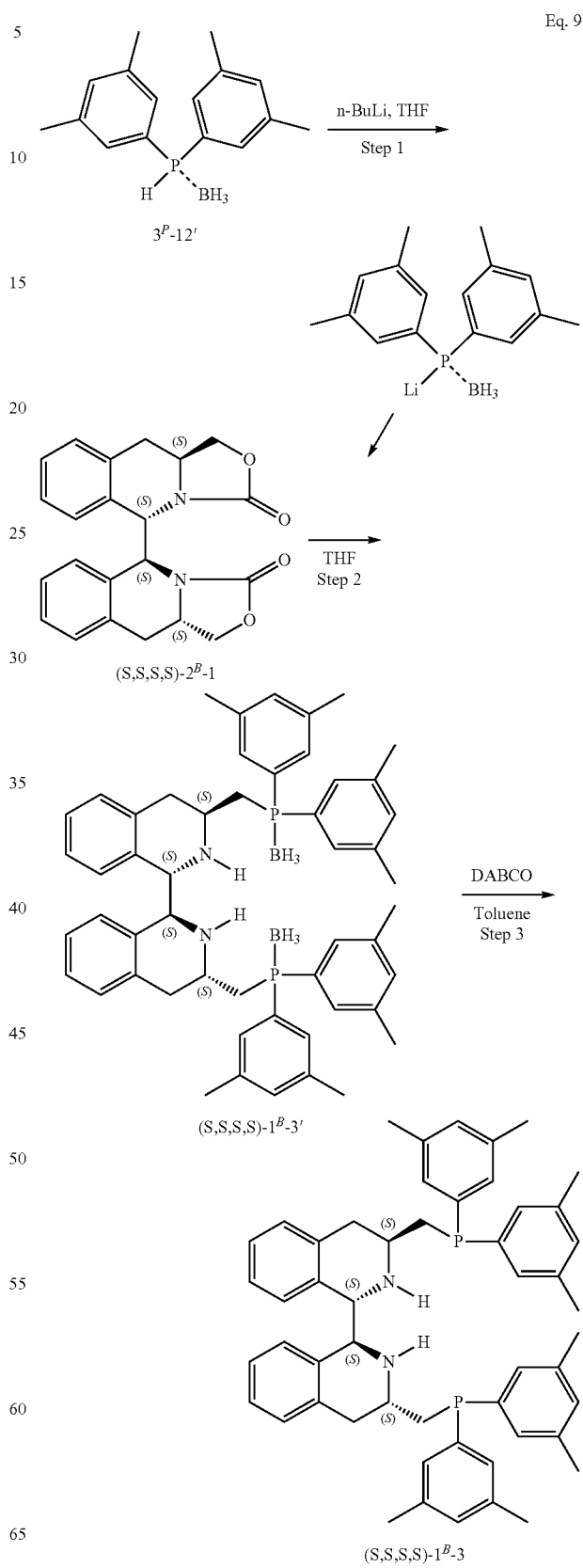

Eq. 9

First step: A 100 mL four-necked round-bottom flask equipped with a magnetic stirring bar, dropping funnel, thermometer, and a three-way stopcock was evacuated and filled with nitrogen gas. Bis(3,5-dimethylphenyl)phosphine-borane ($3^P$-12') (6.0 g, 23.4 mmol, 2.1 equivalents) and dehydrated THF (47 mL) were charged into the flask successively, and the obtained solution was cooled to 5° C. by means of an ice-water bath while stirring with a magnetic stirrer. Subsequently, an n-hexane solution of n-BuLi. (concentration: 2.65 mol/L, 8.8 mL, 23.4 mmol, 2.1 equivalents) was charged into the dropping funnel, and added dropwise into the solution over 20 minutes at a rate keeping the inner temperature at 10° C. or less while stirring the solution. Thereafter, the ice-water bath was removed, and the obtained solution was stirred for one hour at room temperature to give a THF/n-hexane solution lithium bis(3,5-dimethylphenyl)phosphide-borane (23.4 mmol, 2.1 equivalents) as an orange liquid.

Second step: A 500 mL four-necked round-bottom flask equipped with a magnetic stirring bar, condenser, dropping funnel, thermometer, and a three-way stopcock was evacuated and filled with nitrogen gas. The intermediate ((S,S,S,S)-$2^B$-1) obtained in Example 1 (4.2 g, 11.2 mmol, 1.0 equivalent) and dehydrated THF (22 mL) were charged into the flask successively, and the obtained suspension was heated by means of an oil bath while stirring with a magnetic stirrer thereby reflux. Subsequently, the n-hexane/THF solution of lithium bis(3,5-dimethylphenyl)phosphide-borane (23.4 mmol, 2.1 equivalents) prepared in the first step was charged into the dropping funnel, and added dropwise into the suspension over 20 minutes under reflux while stirring, and then the obtained reaction mixture was stirred for one hour under reflux. The reaction mixture was concentrated under reduced pressure, toluene (150 mL) and water (150 mL) were added thereinto successively, followed by stirring, and after leaving to stand, the aqueous layer was separated. The obtained organic layer was washed with water (50 mL) and then concentrated under reduced pressure to give a crude product (11.2 mmol, 1.0 equivalent) of the compound ((S,S,S,S)-$1^B$-3').

$^{31}$P NMR (161 MHz, CDCl$_3$): δ=11.13 (br s, 2 P).

Third step: A 200 mL four-necked round-bottom flask equipped with a magnetic stirring bar, condenser, thermometer, and a three-way stopcock was evacuated and filled with nitrogen gas. The crude product (11.1 mmol, 1.0 equivalent) of the compound ((S,S,S,S)-$1^B$-2') prepared in the second step, toluene (100 mL), and DARCO (3.7 g, 33.3 mmol, 3.0 equivalents) were charged into the flask successively, the obtained cream-colored slurry was heated by means of an oil bath while stirring with a magnetic stirrer, and the mixture was stirred for one hour under reflux. The reaction mixture was cooled to room temperature, washed with water (50 mL), and then concentrated under reduced pressure. The obtained residue was purified by silica gel column chromatography (eluent: toluene/ethyl acetate/triethylamine=100/5/1) to give a target compound ((S,S,S,S)-$1^B$-3) as an orange viscous liquid. Yield: 7.7 g, purity: 79.3% (an impurity was toluene), net weight: 7.7 g, isolated yield: 89.6%. Since the compound had extremely high viscosity, the compound was diluted with toluene to prepare the solution thereof (concentration: about 25%) to facilitate handling, and then stored under nitrogen atmosphere.

$^1$H NMR (400 MHz, CD$_2$Cl$_2$): δ=7.28-6.87 (m, 20H), 4.47 (s, 2H), 3.37-3.26 (m, 2H), 2.92 (dd, J=4.8, 16.0 Hz, 2H), 2.57 (dd, J=6.9, 16.0 Hz, 2H), 2.23 (s, 24H), 2.13 (d, J=7.2 Hz, 4H), 1.70 (br s, 2H).

$^{31}$P NMR (161 MHz, CD$_2$Cl$_2$): δ=−24.57 (s, 2 P)).

[Example 7] Synthesis of Compound ((S,S,S,S)-$1^B$-4') (Eq. 10)

[Chem. 26]

Eq. 10

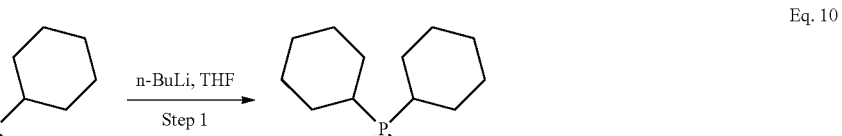

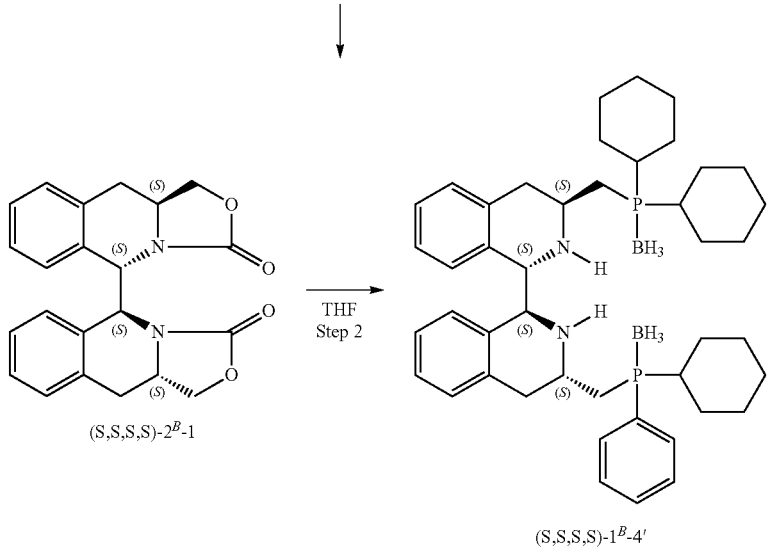

First step: A 100 mL four-necked round-bottom flask equipped with a magnetic stirring bar, dropping funnel, thermometer, and a three-way stopcock was evacuated and filled with nitrogen gas. Dicyclohexylphosphine-borane (3$^P$-6') (5.0 g, 23.6 mmol, 2.1 equivalents) and dehydrated THF (47 mL) were charged into the flask successively, and the obtained solution was cooled to 5° C. by means of an ice-water bath while stirring with a magnetic stirrer. Subsequently, an n-hexane solution of n-BuLi (concentration: 2.65 mol/L, 8.9 mL, 23.6 mmol, 2.1 equivalents) was charged into the dropping funnel, and added dropwise into the solution over 20 minutes at a rate keeping the inner temperature at 10° C. less while stirring the solution. Thereafter, the ice-water bath was removed, and obtained solution was stirred for one hour at room temperature to give an n-hexane/THF solution of lithium dicyclohexylphosphide-borane (23.6 mmol, 2.1 equivalents) as a light-yellow liquid.

Second step: A 500 mL four-necked round-bottom flask equipped with a magnetic stirring bar, condenser, dropping funnel, thermometer, and a three-way stopcock was evacuated and filled with nitrogen gas. The intermediate ((S,S,S,S)-2$^B$-1) obtained in Example 1 (4.2 g, 11.2 mmol, 1.0 equivalent) and dehydrated THF (22 mL) were charged into the flask successively, and the obtained suspension was heated by means of an oil bath while stirring with a magnetic stirrer thereby reflux. Subsequently, an n-hexane/THF solution of lithium dicyclohexylphosphide-borane (23.6 mmol, 2.1 equivalents) prepared in the first step was charged into the dropping funnel, and added dropwise into the suspension over 30 minutes under reflux while stirring, and then the obtained reaction mixture was stirred for one hour under reflux. The reaction mixture was concentrated under reduced pressure, water (150 mL) and CHCl$_3$ (150 mL) were added thereinto successively, followed by stirring, and after leaving to stand, the organic layer was separated. The aqueous layer was extracted with CHCl$_3$ (50 mL), and the organic layers were combined and washed with water (50 mL) and then concentrated under reduced pressure. The obtained residue was purified by silica gel column chromatography (eluent: toluene/ethyl acetate/triethylamine=100/10/1) to give a target compound ((S,S,S,S)-1$^B$-4') as a yellow viscous liquid. Yield: 9.1 g, purity: 78.2% (an impurity was toluene), net weight: 7.2 g, isolated yield: 89.6%. Since the compound had extremely high viscosity, the compound was diluted with toluene to prepare the solution thereof (concentration: about 25%) to facilitate handling, and then stored under nitrogen atmosphere.

$^1$H NMR (400 MHz, CD$_2$Cl$_2$): δ=7.27-7.00 (m, 6H), 6.84 (d, J=7.6 Hz, 2H), 4.47 (s, 2H), 3.73-3.61 (m, 2H), 3.13 (dd, J=4.8, 16.0 Hz, 2H), 2.60 (dd, J=6.0, 16.0 Hz, 2H), 2.00-1.06 (m, 50H), 0.26 (br d, J=110.0 Hz, 6H).
$^{31}$P NMR (161 MHz, CDCl$_3$): δ=22.1 (br s, 2 P).

[Example 8] Synthesis of Compound ((S,S,S,S)-1$^B$-5) (Eq. 11)

[Chem. 27]

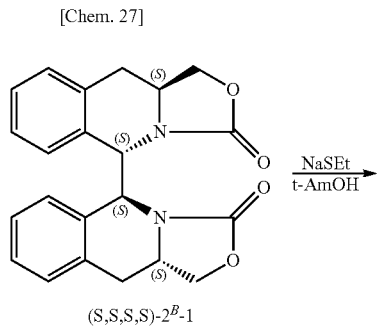

(S,S,S,S)-2$^B$-1

Eq. 11

NaSEt
t-AmOH

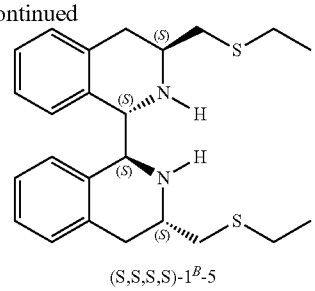

(S,S,S,S)-1$^B$-5

A 200 mL four-necked round-bottom flask equipped with a magnetic stirring bar, condenser, thermometer, and a three-way stopcock was evacuated and filled with nitrogen gas, and the intermediate obtained in Example 1 ((S,S,S,S)-2$^B$-1) (5.0 g, 13.3 mmol, 1.0 equivalent), sodium ethanethiolate (NaSEt) (2.8 g, 33.3 mmol, 2.5 equivalents) and dehydrated 2-methyl-2-butanol (t-AmOH) (100 mL) were charged into the flask successively. The obtained light-pink suspension was heated by means of an oil bath and stirred with a magnetic stirrer for 3 hours under reflux. Thereafter, the reaction solution was cooled to room temperature, added with water (50 mL) and stirred, and then left to stand to separate an aqueous layer. The aqueous layer was extracted once with ethyl acetate (10 mL), then the organic layers were combined and concentrated under reduced pressure, and the obtained residue was purified by silica gel column chromatography (eluent: toluene/ethyl acetate/triethylamine=75/25/1) to give a target compound ((S,S,S,S)-1$^B$-5) as a cream-colored powder. Yield: 3.64 g, isolated yield: 66.3%.

$^1$H NMR (400 MHz, CDCl$_3$): δ=7.20-7.10 (m, 4H), 7.10-7.03 (m, 2H), 6.82 (d, J=7.6 Hz, 2H), 4.47 (s, 2H), 3.57-3.47 (m, 2H), 3.05 (dd, J=4.8, 16.4 Hz, 2H), 2.66 (dd, J=5.2, 13.2 Hz, 2H), 2.63 (dd, J=7.6, 16.4 Hz, 2H), 2.53 (dd, J=8.8, 13.2 Hz, 2H), 2.50 (q, J=7.6 Hz, 4H), 1.64 (br s, 2H), 1.21 (t, J=7.6 Hz, 3H).
$^{13}$C NMR (100 MHz, CDCl$_3$): δ=135.2, 135.0, 129.3, 127.8, 126.5, 125.3, 57.6, 47.9, 37.1, 34.8, 26.3, 14.8.

[Example 9] Syntheses of Compound (S,S,S,S)-1$^B$-6) (Eq. 12)

[Chem. 28]

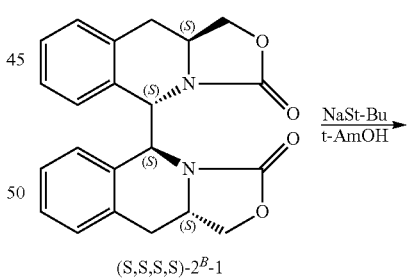

(S,S,S,S)-2$^B$-1

Eq. 12

NaSt-Bu
t-AmOH

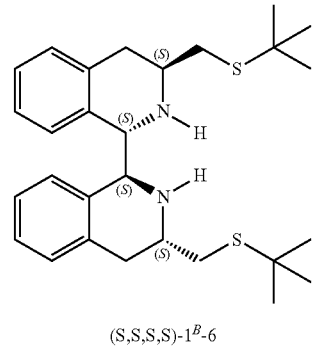

(S,S,S,S)-1$^B$-6

A 200 mL four-necked round-bottom flask equipped with a magnetic stirring bar, condenser, thermometer, and a three-way stopcock was evacuated and filled with nitrogen gas, and the intermediate obtained in Example 1 ((S,S,S,S)-$2^B$-1) (4.0 g, 1.6 mmol, 1.0 equivalent), sodium 2-methyl-2-propanethiolate (NaSt-Bu) (3.0 g, 26.5 mmol, 2.5 equivalents), and dehydrated t-AmOH (80 mL) were charged into the flask successively. The obtained cream-colored suspension was heated by means of an oil bath and stirred with a magnetic stirrer for 3 hours under reflux. Thereafter, the reaction mixture was cooled to room temperature, added with water (40 mL) and stirred, and then left to stand to separate an aqueous layer. The aqueous layer was extracted once with ethyl acetate (10 mL), then the organic layers were combined and concentrated under reduced pressure, and the obtained residue was purified by silica gel column chromatography (eluent: toluene/ethyl acetate/triethylamine=80/20/1) to give a target compound ((S,S,S,S)-$1^B$-6) as a cream-colored powder. Yield: 2.05 g, isolated yield: 41.3%.

$^1$NMR (400 MHz, CDCl$_3$): δ=7.18-7.08 (m, 4H), 7.05-6.97(m, 2H), 6.67 (d, J=8.0 Hz, 2H), 4.38 (s, 2H), 3.53-3.43 (m, 2H), 3.07 (dd, J=4.8, 16.4 Hz, 2H), 2.71-2.56 (m, 6H), 1.65 (br s, 2H), 1.10 (s, 18H).

$^{13}$C NMR (100 MHz, CDCl$_3$): δ=135.2, 135.0, 129.2, 128.3, 126.5, 125.0, 57.8, 48.5, 42.1, 35.0, 34.1, 31.1.

[Example 10] Synthesis of {Fe[R(S,S,S,S)-$1^B$-1](CH$_3$CN)$_2$}(BF$_4$)$_2$ (Eq. 13)

[Chem. 29]

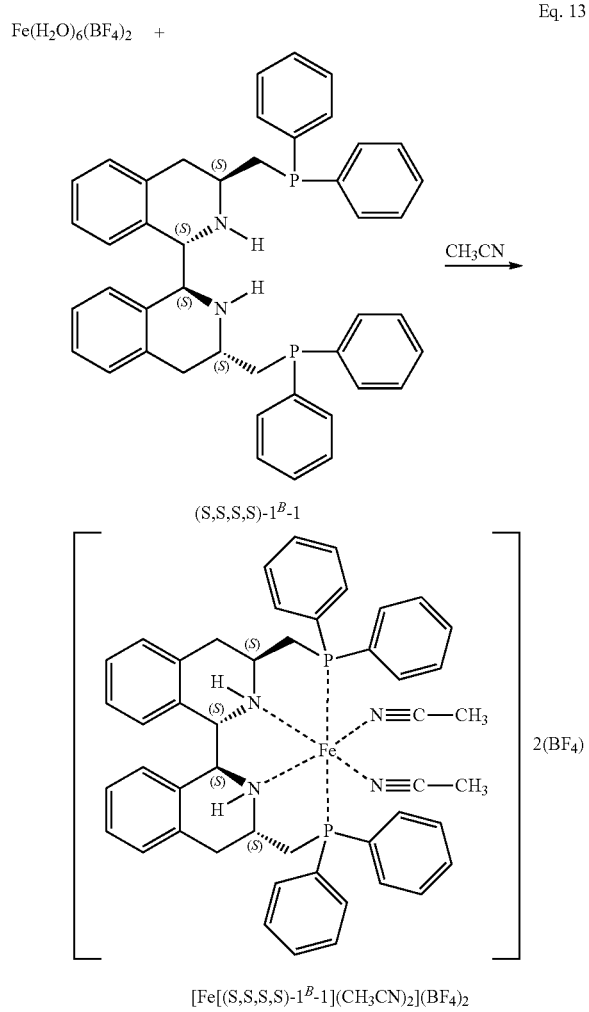

A 100 mL four-necked round-bottom flask equipped with a magnetic stirring bar, condenser, thermometer and a three-way stopcock was evacuated and filled with nitrogen gas. A toluene solution of the compound ((S,S,S,S)-$1^B$-1) (purity: 24.9%, 10.6 g, net weight: 2.64 g, 4.00 mmol, 1.05 equivalents) obtained in Example 3, dehydrated acetonitrile (CH$_3$CN) (38 mL) and iron (II) tetrafluoroborate hexahydrate (Fe(H$_2$O)$_6$(BF$_4$)$_2$) (1.29 g, 3.81 mmol, 1.0 equivalent) were charged into the flask successively, and the obtained purple solution was heated by means of an oil bath while stirring with a magnetic stirrer, and stirred for one hour under reflux. The reaction mixture was concentrated under reduced pressure, and the obtained residue was recrystallized from CH$_3$CN (8 mL)/diethylether (Et$_2$O) (38 mL) to give a target iron complex {Fe[(S,S,S,S)-$1^B$-1](CH$_3$CN)$_2$}(BF$_4$)$_2$ as a reddish-purple powder. Yield: 3.28 g, isolated yield: 88.5%.

$^1$H NMR (400 MHz, CD$_3$CN): δ=7.63-7.00 (m, 25H), 6.97 (d, J=8.0 Hz, 1H), 6.92-6.85 (m, 2H), 5.68 (t, J=10.8 Hz, 1H), 5.08-4.95 (m, 1H), 5.06 (1, J=10.0 Hz, 1H), 4.50 (dd, J=10.0, 12.4 Hz, 1H), 3.78-3.60 (m, 3H), 3.48-2.94 (m, 7H), 1.95 (s, 6H), $^{31}$P NMR (161 MHz, CD$_3$CN): δ=61.30 (d, J=30.5 Hz, 1 P), 57.79 (d, J=30.5 Hz, 1 P).

[Example 11] Synthesis {Fe[(S,S,S,S)-$1^B$-2](CH$_3$CN)$_2$}(BF$_4$)$_2$ (Eq. 14)

[Chem. 30]

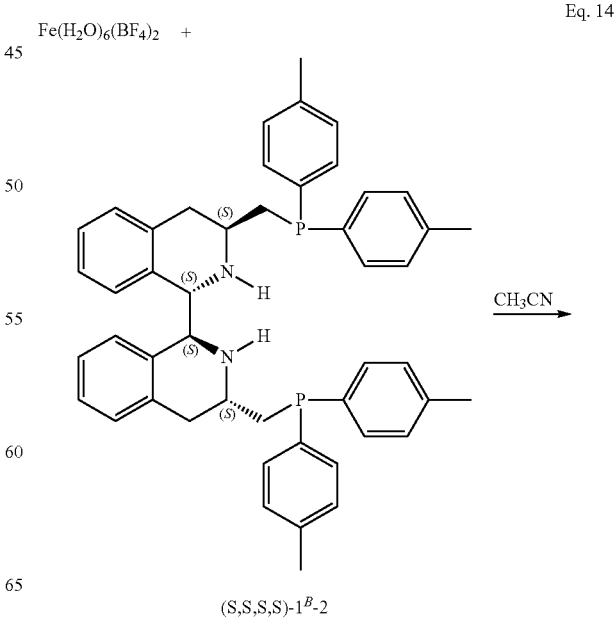

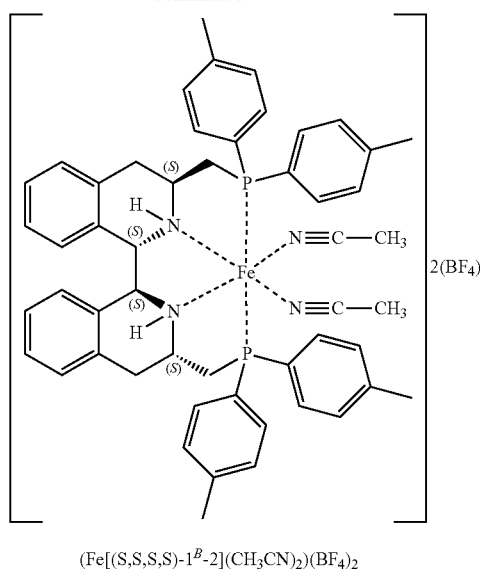

(Fe[(S,S,S,S)-1$^B$-2](CH$_3$CN)$_2$)(BF$_4$)$_2$

A 100 mL four-necked round-bottom flask equipped with a magnetic stirring bar, condenser, thermometer and a three-way stopcock was evacuated and filled with nitrogen was. A toluene solution of the compound ((S,S,S,S)-1$^B$-2) (purity: 24.6%, 4.07 g, net weight: 1.00 g, 1.39 mmol, 1.05 equivalents) obtained in Example 5, dehydrated CH$_3$CN (26 mL) and Fe(H$_2$O)$_6$(BF$_4$)$_2$ (448 g, 1.32 mmol, 1.0 equivalent) were charged into the flask successively, and the obtained reddish-purple solution was heated by means of an oil bath while stirring with a magnetic stirrer, and stirred for one hour under reflux. The reaction mixture was concentrated under reduced pressure, and the obtained residue was recrystallized from CH$_3$CN (1 mL)/Et$_2$O (20 mL) to give a target iron complex {Fe[(S,S,S,S)-1$^B$-2](CH$_3$CN)$_2$}(BF$_4$)$_2$ as a reddish-purple powder. Yield: 1.18 g, isolated yield: 86.9%.

$^1$H NMR (400 MHz, CD$_3$CN): δ=7.50-7.02 (m, 17H), 7.00-6.83 (m, 5H), 6.71 (t, J=9.2 Hz, 2H), 5.59 (t, J=10.4 Hz, 1H), 5.02 (t, J=9.6 Hz, 1H), 5.00-4.86 (m, 1H), 4.47 (t, J=11.2 Hz, 1H), 3.76-3.50 (m, 3H), 3.46-3.14 (m, 5H), 3.10-2.88 (m, 2H), 2.42 (s, 3H), 2.38 (s, 3H), 2.30 (s, 3H), 2.24 (s, 3H), 1.95 (s, 6H).

$^{31}$P NMR (161 MHz, CD$_3$CN): δ=60.18 (d, J=31.5 Hz, 1 P), 56.49 (d, J=31.5 Hz, 1 P).

[Example 12] Synthesis of {Fe[(S,S,S,S)-1$^B$-3](CH$_3$CN)$_2$}(BF$_4$)$_2$ (Eq. 15)

[Chem. 31]

Fe(H$_2$O)$_6$(BF$_4$)$_2$   +    Eq. 15

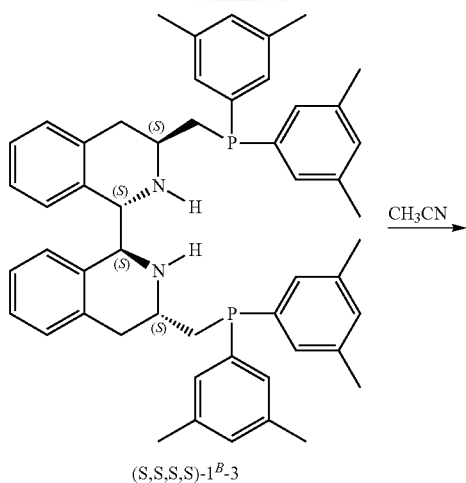

(S,S,S,S)-1$^B$-3

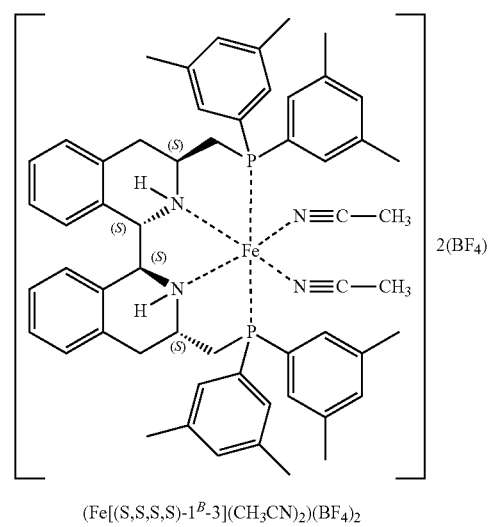

(Fe[(S,S,S,S)-1$^B$-3](CH$_3$CN)$_2$)(BF$_4$)$_2$

A 100 mL four-necked round-bottom flask equipped with a magnetic stirring bar, condenser, thermometer and a three-way stopcock was evacuated and filled with nitrogen gas. A toluene solution of the compound ((S,S,S,S)-1$^B$-3) (purity: 24.8%, 4.03 g, net weight: 1.00 g, 1.29 mmol, 1.05 equivalents) obtained in Example 6, dehydrated CH$_3$CN (25 mL), and Fe(H$_2$O)$_6$(BF$_4$)$_2$ (416 g, 1.23 mmol, 1.0 equivalent) were charged into the flask successively, and the obtained purple solution was heated by means of an oil bath while stirring with a magnetic stirrer, and stirred for one hour under reflux. The reaction mixture was concentrated under reduced pressure, and the obtained residue was triturated, washed with Et$_2$O (25 mL), and then dried in vacuo to give a target iron complex {Fe[(S,S,S,S)-1$^B$-3](CH$_3$CN)$_2$}(BF$_4$)$_2$ as a purple powder. Yield: 1.22 g, isolated yield: 91.5%.

$^1$H NMR (400 MHz, CH$_3$CN): δ=7.52-6.92 (m, 16H), 6.61 (t, J=9.6 Hz, 4H), 5.54 (t, J=10.8 Hz, 1H), 5.02 (t, J=9.6 Hz, 1H), 4.92-4.77 (m, 1H), 4.46 (t, J=10.8 Hz, 1H), 3.76 (dd, J=5.2, 14.8 Hz, 1H), 3.68-3.06 (m, 8H), 2.94-2.76 (m, 1H), 2.34 (s, 6H), 2.25 (s, 6H), 2.08 (s, 6H), 1.97 (s, 6H), 1.95 (s, 6H).

$^{31}$P NMR (161 MHz, CD$_3$CN): δ=59.81 (d, J=30.9 Hz, 1 P), 53.78 (d, J=30.9 Hz, 1 P).

[Example 13] Synthesis {Fe[(S,S,S,S)-1$^B$-1](t-OcNC)(Ch$_3$CN)}(BF$_4$)$_2$ (Eq. 16)

[Chem. 32]

Eq. 16

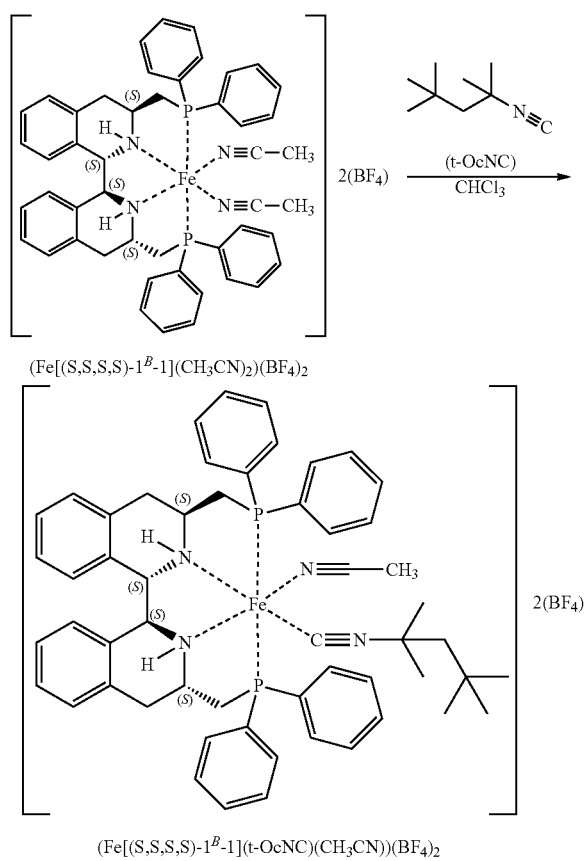

(Fe[(S,S,S,S)-1$^B$-1](CH$_3$CN)$_2$)(BF$_4$)$_2$ (Fe[(S,S,S,S)-1$^B$-1](t-OcNC)(CH$_3$CN))(BF$_4$)$_2$

A 100 mL four-necked round-bottom flask equipped with a magnetic stirring bar, dropping funnel, thermometer and a three-way stopcock was evacuated and filled with nitrogen gas. 1,1,3,3-tetramethylbutylisocyanate (t-OcNC) (716 mg, 5.15 mmol, 5.0 equivalents), dehydrated CHCl$_3$ (10 mL) and Fe[(S,S,S,S)-1$^B$-1](CH$_3$CN)$_2$](BF$_4$)$_2$ (1.00 g, 1.03 mmol, 1.0 equivalent) obtained in Example 10 were charged into the flask successively, and the obtained reddish-purple solution was stirred with a magnetic stirrer at room temperature for one hour. Subsequently, diethylether (20 mL) was charged into the dropping funnel, and added dropwise into the flask over 10 minutes at room temperature while stirring, the reaction mixture, and a precipitated crude crystal was filtered by suction. The crude crystal was recrystallized from CH$_3$CN (4 mL)/Et$_2$O (40 mL) to give a target iron complex {Fe[(S,S,S,S)-1$^B$-1] (t-OcNC)(CH$_3$CN)}(BF$_4$)$_2$ as an orange powder.

Yield: 782 mg, isolated yield: 70.9%.

$^1$H NMR (400 MHz, CD$_3$CN): δ=7.67-7.25 (m, 21H), 7.21 (dt, J=1.2, 7.6 Hz, 1H), 7.16-7.08 (m, 2H), 7.02 (d, J=7.6 Hz, 1H), 6.98 (d, J=8.0 Hz, 1H), 6.88-6.79 (m, 2H), 5.20-5.00 (m, 2H), 4.98 (t, J=9.6 Hz, 1H), 4.59 (dd, J=10.4, 12.0 Hz, 1H), 3.66-3.28 (m, 6H), 3.26-3.06 (m, 3H), 2.64 (dt, J=3.2, 14.0 Hz, 1H), 1.54 (s, 3H), 1.12 (d, J=14.8 Hz, 1H), 1.03 (d, J=14.8 Hz, 1H), 0.95 (s, 3H), 0.88 (s, 3H), 0.70 (s, 9H).

$^{31}$P NMR (161 MHz, CD$_3$CN): δ=58.76 (d, J=30.9 Hz, 1 P), 56.08 (d, J=30.9 Hz, 1 P).

[Example 14] Synthesis of {Fe[(S,S,S,S)-1$^B$-1](AdNC)(CH$_3$CN)}(BF$_4$)$_2$(Eq. 17)

[Chem. 33]

Eq. 17

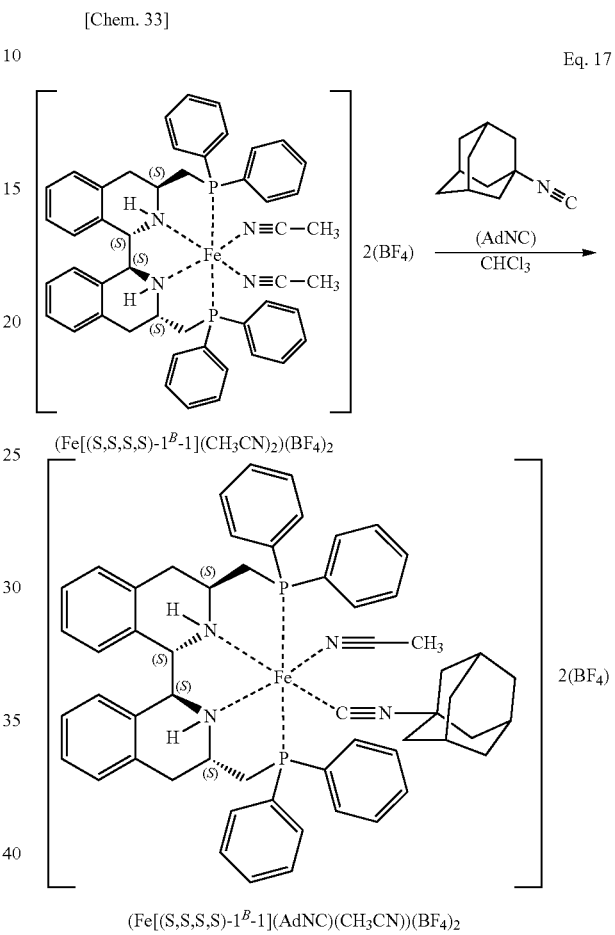

(Fe[(S,S,S,S)-1$^B$-1](CH$_3$CN)$_2$)(BF$_4$)$_2$ (Fe[(S,S,S,S)-1$^B$-1](AdNC)(CH$_3$CN))(BF$_4$)$_2$

A 100 mL four-necked round-bottom flask equipped with a magnetic stirring bar, dropping funnel, thermometer and a three-way stopcock was evacuated and filled with nitrogen gas. 1-isocyanoadamantane (AdNC) (1.0 g, 6.20 mmol, 5.0 equivalents), dehydrated CHCl$_3$ (25 mL) and Fe[(S,S,S,S)-1$^B$-1](CH$_3$CN)$_2$](BF$_4$)$_2$ (1.21 g, 1.24 mmol, 1.0 equivalent) obtained in Example 10 were charged into the flask successively, and the obtained reddish-purple solution was stirred at room temperature for one hour with a magnetic stirrer. Subsequently, diethylether (25 mL) was charged into the dropping funnel, and added into the flask 10 minutes at room temperature while stirring the reaction mixture, and a precipitated crude crystal was filtered by suction. The crude crystal was recrystallized from CH$_3$CN (12 mL)/Et$_2$O (36 mL) to give a target iron complex {Fe[(S,S,S,S)-1$^B$-1] (AdNC)(CH$_3$CN)}(BF$_4$)$_2$ as an orange powder. Yield: 1.06 g, isolated yield: 78.2%.

$^1$H NMR (400 MHz, CD$_3$CN): δ=7.65-7.24 (m, 21H), 7.21 (dt, J=1.6, 8.0 Hz, 1H), 7.15-7.07 (m, 2H), 7.01 (d, J=7.6 Hz, 1H), 6.98 (d, J=8.0 Hz, 1H), 6.86-6.79 (m, 2H), 5.23 (t, J=10.4 Hz, 2H), 4.94 (t, J=10.0 Hz, 1H), 4.57 (dd, J=10.4, 12.0 Hz, 1H), 3.62-3.05 (m, 9H), 2.63 (dt, J=3.6, 14.4 Hz, 1H), 1.80 (m, 3H), 1.55 (s, 3H), 1.52-1.43 (m, 3H), 1.40-1.26 (m, 9H).

$^{31}$P NMR (161 MHz, CD$_3$CN): δ=59.39 (d, J=30.9 Hz, 1 P), 56.33 (d, J=30.9 Hz, 1 P).

[Example 15] Synthesis of {Fe[(S,S,S,S)-1$^B$-1](AdNC)$_2$}(BF$_4$)$_2$ (Eq. 18)

[Chem. 34]

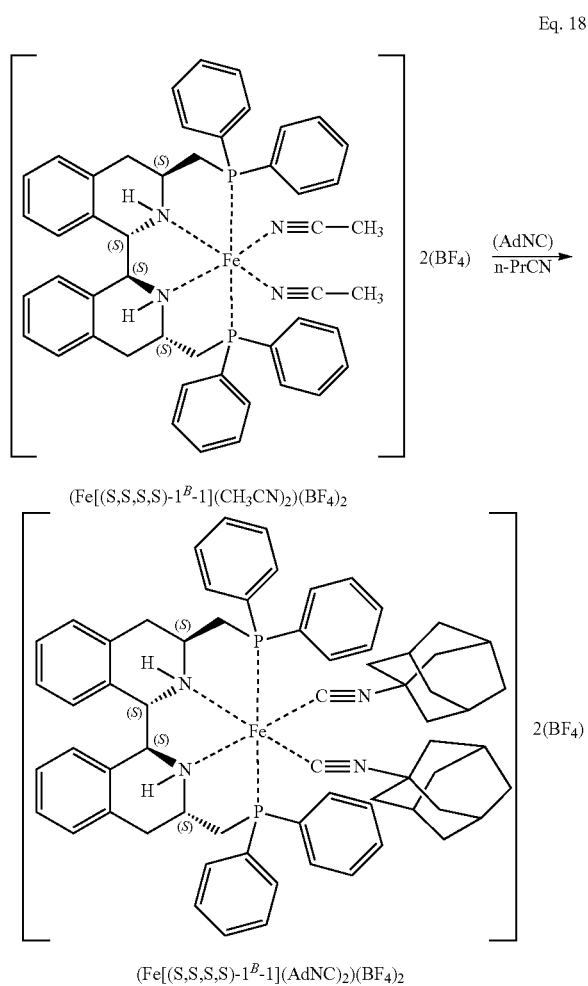

(Fe[(S,S,S,S)-1$^B$-1](CH$_3$CN)$_2$)(BF$_4$)$_2$ (Fe[(S,S,S,S)-1$^B$-1](AdNC)$_2$)(BF$_4$)$_2$

A 30 mL three-necked round-bottom flask equipped with a magnetic stirring bar, condenser, thermometer and a three-way stopcock was evacuated and filled with nitrogen gas. {Fe[(S,S,S,S)-1$^B$-1](CH$_3$CN)$_2$}(BF$_4$)$_2$ (482 mg, 0.496 mmol, 1.0 equivalent) obtained in Example 10, AdNC (200 mg, 1.24 mmol, 2.5 equivalents) and butyronitrile (n-PrCN) (5 mL) were charged into the flask successively, and the obtained reddish-purple solution was heated by means of an oil bath while stirring with a magnetic stirrer, and stirred for one hour under reflux. The reaction mixture was concentrated under reduced pressure, and the obtained residue was recrystallized from CHCl$_3$ (5 mL)/Et$_2$O (5 mL) to give a target iron complex {Fe[(S,S,S,S)-1$^B$-1](AdNC)$_2$}(BF$_4$)$_2$ as an orange powder. Yield: 346 mg, purity: 91.0% (including one molecule of CHCl$_3$), isolated yield: 52.3%.

$^1$H NMR (400 MHz, CD$_3$CN): δ=7.62-7.20 (m, 24H), 7.07 (dd, J=3.2, 7.6 Hz, 2H), 7.00-6.92 (m, 2H), 5.32-5.08 (m, 2H), 4.96 (t, J=10.0 Hz, 1H), 4.52 (t, J=11.2 Hz, 1H), 3.62 (dd, J=5.6, 14.8 Hz, 1H), 3.60-3.08 (m, 6H), 2.94 (dt, J=3.6, 14.0 Hz, 1H), 2.86 (dd, J=10.8, 14.8 Hz, 1H), 2.52 (dt, J=3.6, 14.0 Hz, 1H), 1.85-1.71 (m, 6H), 1.53-1.22 (m, 21H), 1.14-1.05 (m, 3H).
$^{31}$P NMR (161 MHz, CD$_3$CN): δ=61.97 (d, J=29.9 Hz, 1 P). 59.70 (d, J=29.9 Hz, 1 P).

[Example 16] Synthesis of {Fe[(S,S,S,S)-1$^B$-1](AdNC)(CH$_3$CN)}Br$_2$ (Eq. 19)

[Chem. 35]

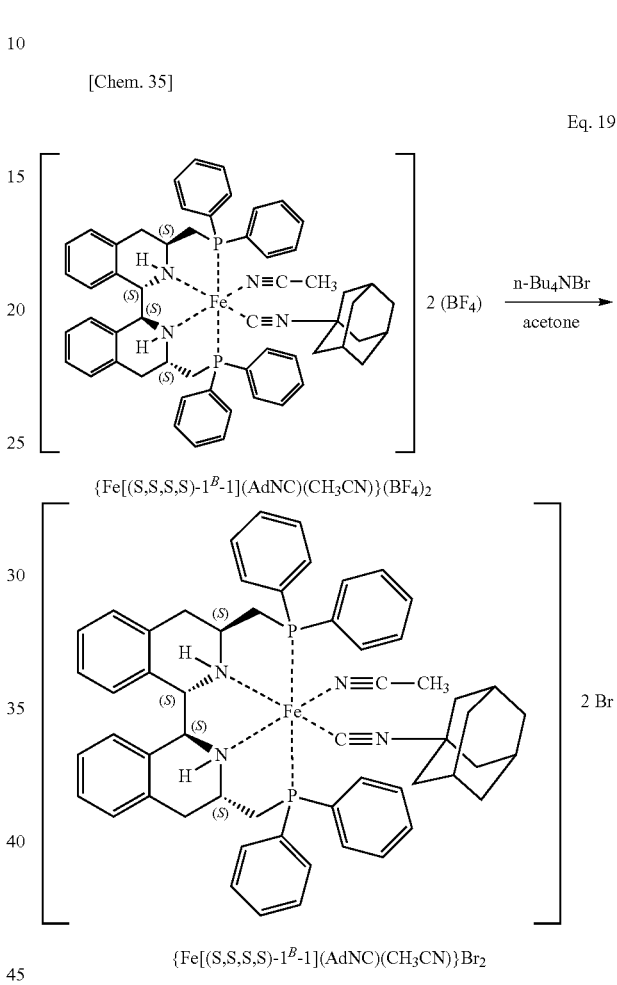

{Fe[(S,S,S,S)-1$^B$-1](AdNC)(CH$_3$CN)}(BF$_4$)$_2$

{Fe[(S,S,S,S)-1$^B$-1](AdNC)(CH$_3$CN)}Br$_2$

A 50 mL four-necked round-bottom flask equipped with a magnetic stirring bar, thermometer and a three-way stopcock was evacuated and filled with nitrogen gas. {Fe[(S,S,S,S)-1$^B$-1](AdNC)(CH$_3$CN)}(BF$_4$)$_2$ (500 mg, 0.458 mmol, 1.0 equivalent; obtained in Example 14, dehydrated acetone (30 mL) and tetrabutylammonium bromide (n-Bu$_4$NBr) (369 mg, 1.15 mmol, 2.5 equivalents) were charged into the flask successively, and the obtained orange solution was stirred with a magnetic stirrer at room temperature for one hour. Precipitated crystals were collected by suction filtration and washed with Et$_2$O/acetone=1/1 mixed solvent (10 mL), and then dried in vacuo to give a target iron complex {Fe[(S,S,S,S)-1$^B$-1](AdNC)(CH$_3$CN)}Br$_2$ as a dull orange powder.
Yield: 376 mg, isolated yield: 76.2%.

$^1$H NMR (400 MHz, CD$_3$CN): δ=7.65-7.45 (m, 10H), 7.45-7.21 (m, 11H), 7.17 (dt, J=1.6, 8.0 Hz, 1H), 7.09 (dt, J=2.0, 8.0 Hz, 2H), 6.99 (d, J=8.0 Hz, 2H), 6.89-6.80 (m, 2H), 5.71 (t, J=10.0 Hz, 1H), 5.05-4.91 (m, 1H), 4.71 (dd, J=10.4, 11.6 Hz, 1H), 4.15 (dd, J=11.6, 14.0 Hz, 1H), 3.67-3.09 (m, 9H), 2.96 (dt, J=3.2, 14.0 Hz, 1H), 1.80-1.73 (m, 3H), 1.63-1.53 (m, 6H), 1.48-1.28 (m, 9H).

$^{31}$P NMR (161 MHz, CD$_3$CN): δ=60.75 (d, J=29.5 Hz, 1 P), 56.88 (d, J=29.5 Hz, 1 P).

[Example 17] Synthesis of RuCl$_2$[(S,S,S,S)-1$^B$-1] (Eq. 20)

[Chem. 36]

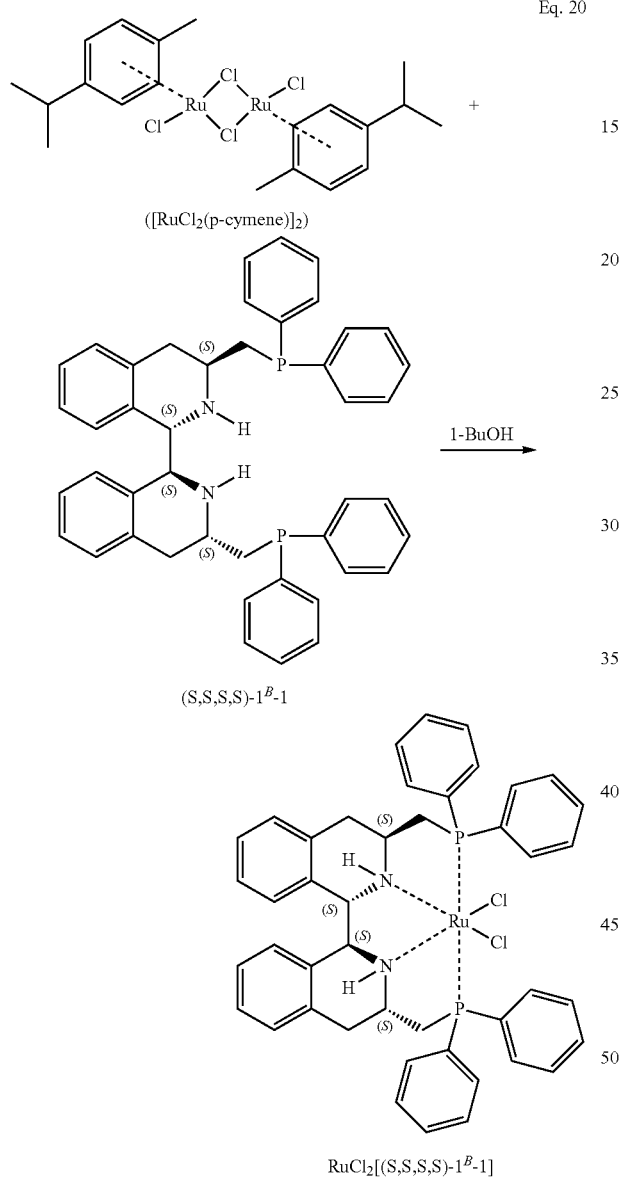

A 200 mL four-necked round-bottom flask equipped with a magnetic stirring bar, condenser, thermometer and a three-way stopcock was evacuated and filled with nitrogen gas. A toluene solution of the compound ((S,S,S,S)-1$^B$-1) (purity: 24.9%, 13.7 g, net weight: 3.4 g, 5.15 mmol, 2.1 equivalents) obtained in Example 3, 1-butanol (1-BuOH) (50 mL) add dichloro(p-cymene)ruthenium(II) dimer ([RuCl$_2$(p-cymene)]$_2$) (1.5 g, 2.45 mmol, 1.0 equivalent) were charged into the flask successively, and the obtained red suspension was heated by means of an oil bath while stirring with a magnetic stirrer and stirred for one hour at 80° C. The obtained orange slurry was cooled to room temperature, then methanol (50 mL) was added, the mixture was cooled to 5° C. by means of an ice-water bath while stirring with a magnetic stirrer, and filtered by suction. The obtained yellowish-orange powder was washed with methanol (20 mL) and then dried by heating in vacuo to give a target ruthenium complex RuCl$_2$[(S,S,S,S)-1$^B$-1] as an yellowish-orange powder. Yield: 1.64 g, isolated yield: 40.3%.

$^1$H NMR (400 MHz, CD$_2$Cl$_2$): δ=8.23-8.13 (m, 2H), 7.58-7.48 (m, 2H), 7.43-6.86 (m, 22H), 6.79 (t, J=7.2 Hz, 1H), 6.41 (d, J=7.6 Hz, 1H), 5.97 (d, J=7.6 Hz, 1H), 5.88 (dd, J=3.2, 11.2 Hz, 1H), 5.11-4.94 (m, 1H), 4.90-4.80 (m, 1H), 3.98-3.82 (m, 1H), 3.58-3.20 (m, 5H), 3.09 (dt, J=2.8, 13.2 Hz, 1H), 2.78 (dd, J=6.4, 12.4 Hz, 1H), 2.64-2.48 (m, 2H).

$^{31}$P NMR (161 MHz, CD$_2$Cl$_2$): δ=60.54 (d, J=29.0 Hz, 1 P), 43.26 (d, J=29.0 Hz, 1 P).

[Example 18] Synthesis of RuCl$_2$[(R,R,R,R)-1$^B$-1] (Eq. 21)

[Chem. 37]

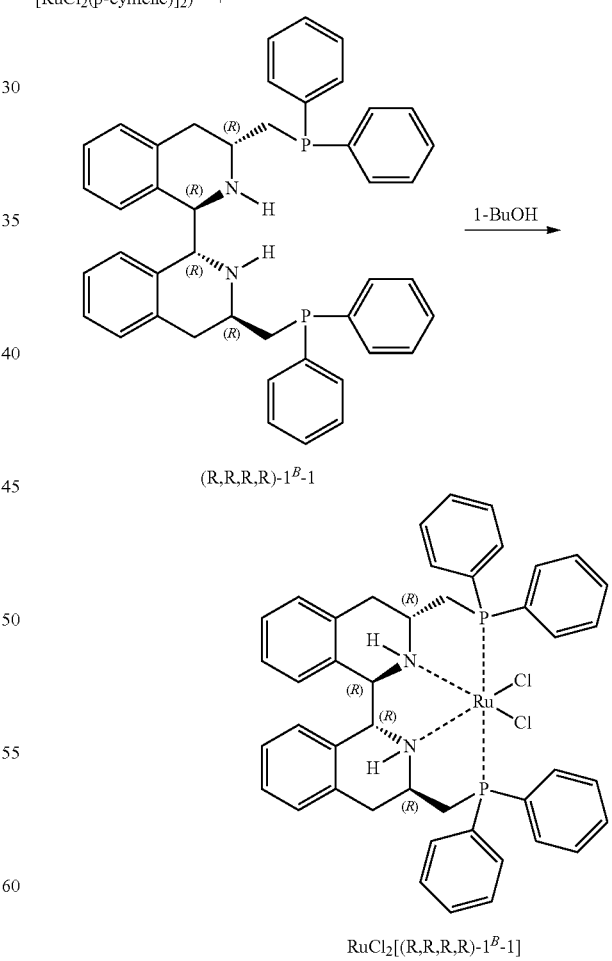

A target ruthenium complex RuCl$_2$[(R,R,R,R)-1$^B$-1] was synthesized in the same manner as in Example 17 except that a toluene solution of the compound ((R,R,R,R)-1$^B$-1)

obtained in Example 4 was used instead of the toluene solution of the compound ((S,S,S,S)-1$^B$-1). Yield: 1.52 g, isolated yield: 37.3% The results of NMR measurement were the same as in Example 17.

[Example 19] Synthesis of RuH(BH$_4$)[(R,R,R,R)-1$^B$-1] (Eq. 22)

[Chem. 38]

Eq. 22

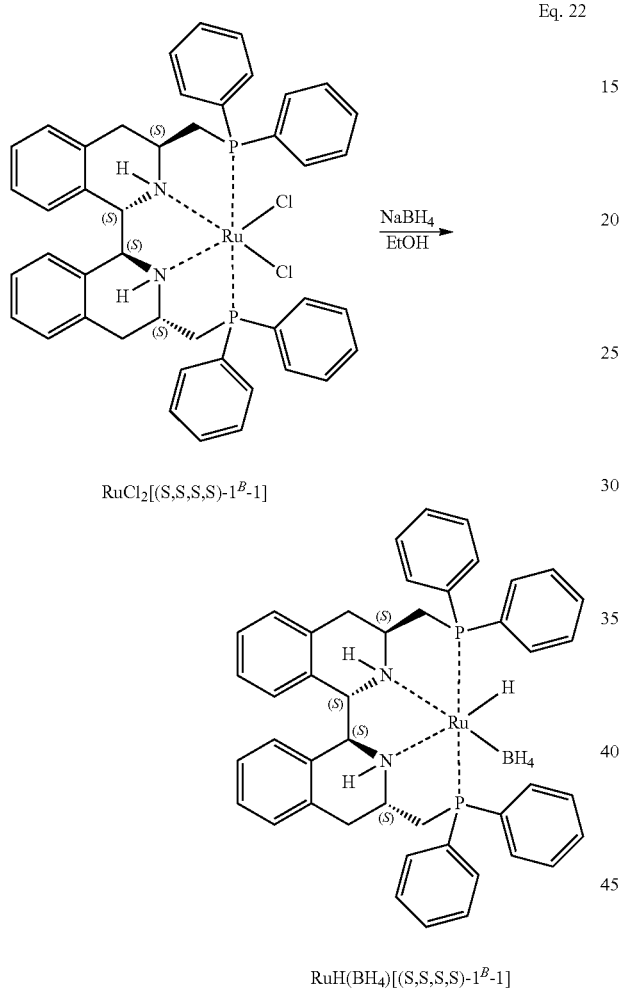

A 100 mL four-necked round-bottom flask equipped with a magnetic stirring bar, condenser, thermometer and a three-way stopcock was evacuated and filled with nitrogen gas. RuCl$_2$[(S,S,S,S)-1$^B$-1] (1.00 g, 1.20 mmol, 1.0 equivalent) obtained in Example 17, dehydrated ethanol (EtOH) (60 mL) and sodium borohydride (NaBH4) (454 mg, 12.00 mmol, 10.0 equivalents) were charged into the flask successively, and the obtained yellowish-orange slurry was heated by means of an oil bath while stirring with a magnetic stirrer, and stirred for one hour under reflux. Thereafter, the condenser was removed from the reactor, a Claisen distillation apparatus was attached to the flask, and 40 mL of EtOH was recovered under atmospheric pressure under a nitrogen stream. The concentrated solution was cooled to 5° C. by means of an ice-water bath, then degassed water (20 mL) was charged into the flask, and precipitated crystals were collected by suction filtration under a nitrogen stream. The crystals were washed with degassed 50% aqueous EtOH (10 mL), degassed water (10 mL) and degassed 50% aqueous EtOH (10 mL) successively, and dried at ambient temperature in vacuo to give a target ruthenium complex RuH(BH$_4$) [(S,S,S,S)-1$^B$-1] as a light-brown powder. Yield: 869 mg, isolated yield: 93.1%.

$^1$H NMR (400 MHz, C$_6$D$_6$): δ=8.38-8.29 (m, 2H), 8.15-8.06 (m, 2H), 7.37-7.26 (m, 4H), 7.24-7.06 (m, 7H), 7.06-6.92 (m, 3H), 6.88-6.70 (m, 8H), 6.66 (dt, J=1.2, 7.6 Hz, 2H), 5.93-5.75 (m, 1H), 5.64-5.46 (m, 1H), 5.01 (t, J=10.0 Hz, 1H), 4.36 (dd, J=10.4, 12.0 Hz, 1H), 3.25-3.09 (m, 1H), 2.78-2.18 (m, 9H), −1.02 (br s, 4H), 14.90 (dd, J=22.0, 26.4 Hz, 1H).

$^{31}$P NMR (161 MHz, C$_6$D$_6$): δ=70.47 (d, J=25.1 Hz, 1 P), 65.08 (d, J=25.1 Hz, 1 P).

[Example 20] Synthesis of RuH(BH$_4$)[(R,R,R,R)-1$^B$-1] (Eq. 23)

[Chem. 39]

Eq. 23

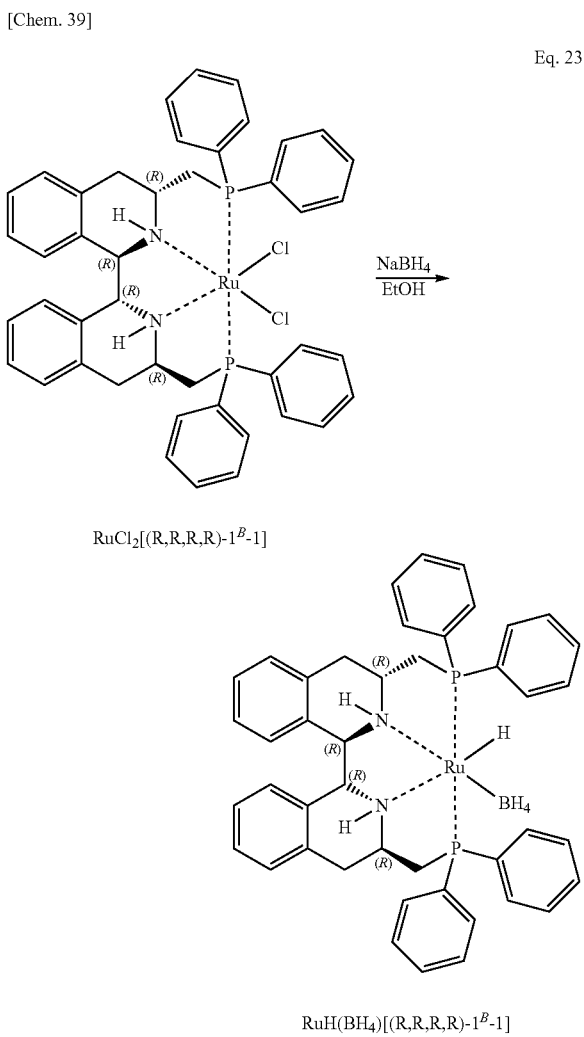

A target ruthenium complex RuH(BH$_4$)[(R,R,R,R)-1$^B$-1] was synthesized in the same manner as in Example 19 except that RuCl$_2$[(S,S,S,S)-1$^B$-1] obtained in Example 18 was used instead of RuCl$_2$[(S,S,S,S)-1$^B$-1]. Yield: 890 mg, isolated yield: 95.4%. The results of NMR measurement were the same as in Example 19.

[Example 21] Production of (R)-2-Phenylethylalcohol by Transfer Hydrogenation Reaction of Acetophenone Using {Fe[S,S,S,S)-1$^B$-1](AdNC)(CH$_3$CN)}(BF$_4$)$_2$ as Catalyst (Eq. 24)

[Chem. 40]

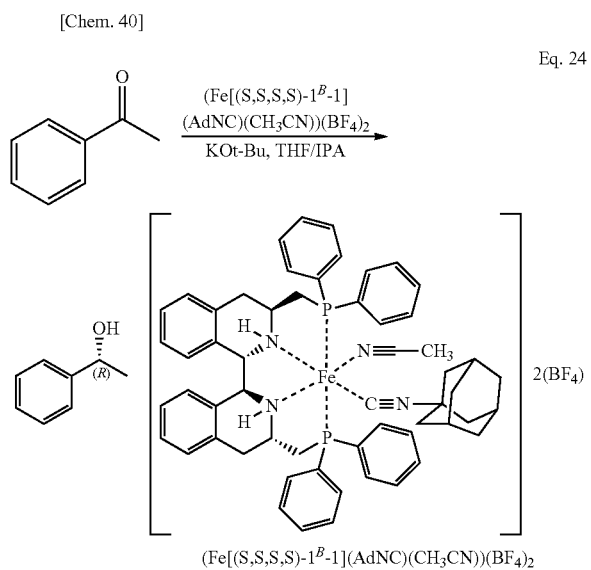

(Fe[(S,S,S,S)-1$^B$-1](AdNC)(CH$_3$CN))(BF$_4$)$_2$

To a 30 mL two-necked round-bottom flask equipped with a magnetic stirring bar and a three-way stopcock, {Fe[S,S,S,S)-1$^B$-1](AdNC)(CH$_3$CN)}(BF$_4$)$_2$ (23.41 mg, 21.4 μmol, 1.0 mol %) obtained in Example 14 was charged, and the inside of the flask was evacuated and filled with nitrogen gas. Subsequently, dehydrated 2-propanol (IPA) (8.6 acetophenone (250 μL, 2.14 mmol, 1.0 equivalent) and a THF solution of potassium tert-butoxide (KOt-Bu) (concentration: 1.0 mol/L, 107 μL, 107.0 μmol, 5.0 mol %) were charged into the flask successively, and the mixture was stirred with a magnetic stirrer at 25° C. for one hour to produce a target (R)-2-phenylethylalcohol. Conversion: 45.6%, selectivity: >99%, optical purity: 89.6% ee (according to GC analysis).

GC retention time (measurement condition 1): acetophenone: 3.01 min, (R)-2-phenylethylalcohol: 5.74 min, (S)-phenylethylalcohol: 6.19 min.

[Example 22] Production of benzyl alcohol by Hydrogenation Reaction of methyl benzoate Using RuCl$_2$[(S,S,S,S)-1$^B$-1] as Catalyst (Eq. 25)

[Chem. 41]

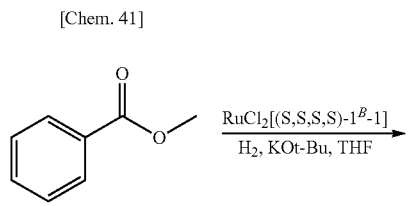

Eq. 25

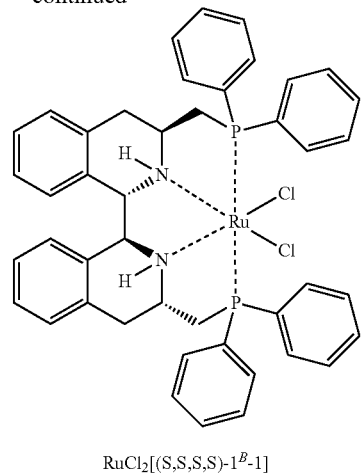

RuCl$_2$[(S,S,S,S)-1$^B$-1]

To a 100 mL stainless steel-made autoclave apparatus equipped with a glass-made inner tube and a magnetic stirring bar was charged RuCl$_2$[(S,S,S,S)-1$^B$-1] (4.2 mg, 5.00 μmol, 0.1 mol %) obtained in Example 17, and the inside of the apparatus was purged with nitrogen gas. Subsequently, dehydrated THF (5.0 mL), methyl benzoate (626 μL, 5.00 mmol, 1.0 equivalent) and a THF solution of KOt-Bu (concentration: 1.0 mol/L, 50 μL, 0.50 mmol, 0.1 equivalent) were charged into the apparatus successively. Furthermore, the inside of the apparatus was replaced by hydrogen gas and the hydrogen pressure was set to 5 MPa, followed by stirring with a magnetic stirrer at 80° C. for 5 hours to produce target benzyl alcohol. Conversion: >99%, selectivity: >99% (according to GC analysis). GC Retention time (measurement condition 2): methyl benzoate: 7.00 minutes, benzyl alcohol: 6.15 minutes.

[Example 23] Production of benzyl alcohol by Hydrogenation Reaction of methyl benzoate Using RuH(BH$_4$)[(S,S,S,S)-1$^B$-1] as Catalyst (Eq. 26)

[Chem. 42]

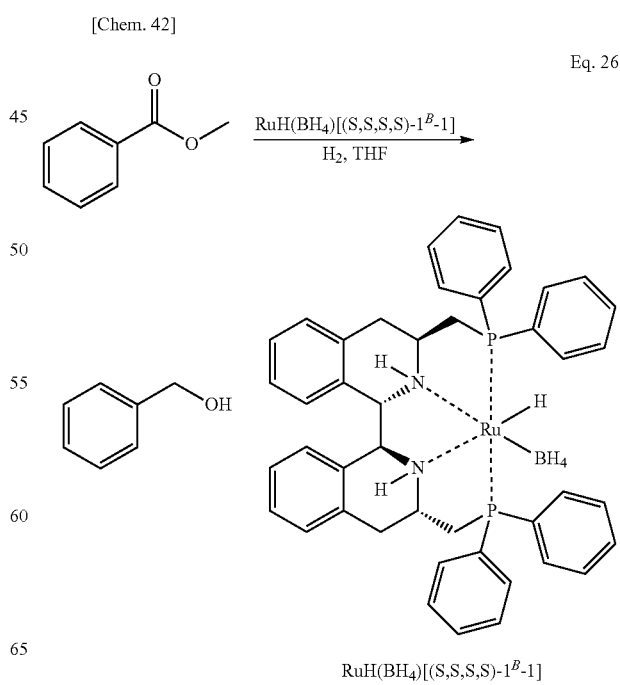

RuH(BH$_4$)[(S,S,S,S)-1$^B$-1]

To a 100 mL stainless steel-made autoclave apparatus equipped with a glass made inner tube and a magnetic stirring bar was charged RuH(BH$_4$)[(S,S,S,S)-1$^B$-1] (4.2 mg, 5.00 µmol, 0.1 mol %) obtained in Example 19, and the inside of the apparatus was purged with nitrogen gas. Subsequently, dehydrated THF (5.0 mL) and methyl benzoate (626 µL, 5.00 mmol, 1.0 equivalent) were charged into the apparatus successively. Furthermore, the inside of the apparatus was replaced by hydrogen gas and the hydrogen pressure was set to 5 MPa, followed by stirring with a magnetic stirrer at 80° C. for 5 hours to produce target benzyl alcohol. Conversion: >99%, selectivity: >99% (according to GC analysis). Measurement conditions and GC retention time in GC analysis refer to Example 22.

[Example 24] Production of (R)-2-Phenylethylalcohol by Hydrogenation Reaction of Acetophenone Using RuCl$_2$[(S,S,S,S)-1$^B$-1] as Catalyst (Eq. 27)

[Chem. 43]

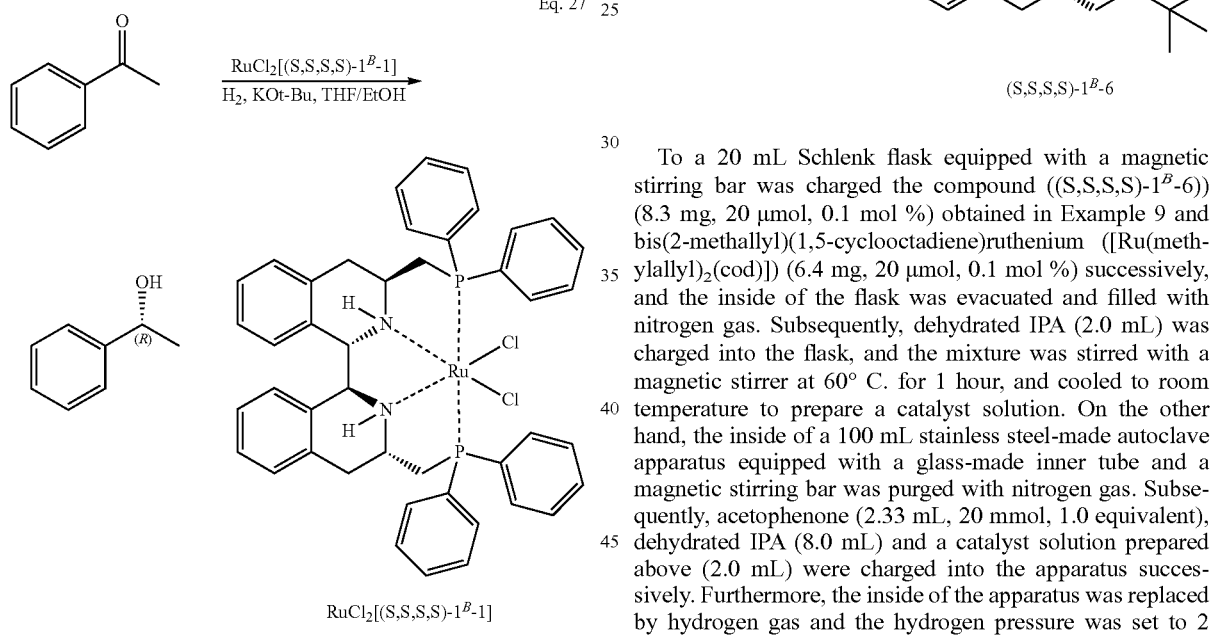

RuCl$_2$[(S,S,S,S)-1$^B$-1]

To a 100 mL stainless steel-made autoclave apparatus equipped with a glass-made inner tube and a magnetic stirring bar was charged RuCl$_2$[(S,S,S,S)-1$^B$-1] (4.2 mg, 5.00 µmol, 0.05 mol %) obtained in Example 17, and the inside of the apparatus was purged with nitrogen gas. Subsequently, dehydrated ethanol (5.0 mL), acetophenone (1.17 mL, 10.0 mmol, 1.0 equivalent), and a THF solution of KOt-Bu (concentration: 1.0 mol/L, 1.0 mL, 1.00 mmol, 0.1 equivalent) were charged into the apparatus successively. Furthermore, the inside of the apparatus was replaced by hydrogen gas and the hydrogen pressure was set to 5 MPa, followed by stirring with a magnetic stirrer at 40° C. for 5 hours to produce target (R)-2-phenylethylalcohol. Conversion: >99%, selectivity: >99%, optical purity: 52.1% ee (according to GC analysis). Measurement conditions and GC retention time of the compound in GC analysis refer to Example 21.

[Example 25] Production of (S)-2-Phenylethylalcohol by Hydrogenation Reaction of Acetophenone Using Compound ((S,S,S,S)-1$^B$-6) as Ligand (Eq. 28)

[Chem. 44]

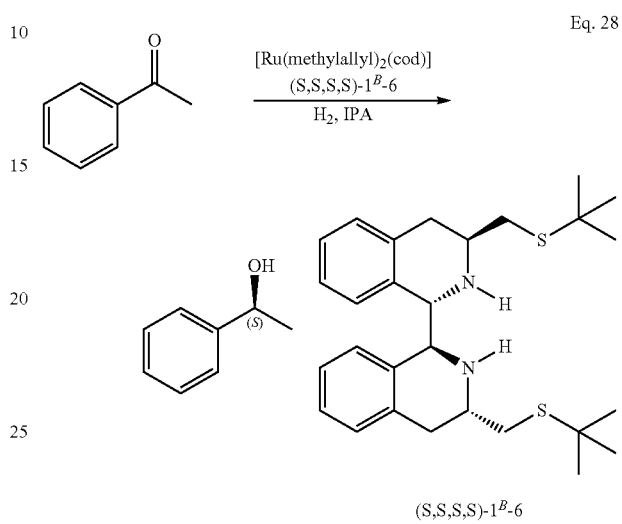

(S,S,S,S)-1$^B$-6

To a 20 mL Schlenk flask equipped with a magnetic stirring bar was charged the compound ((S,S,S,S)-1$^B$-6)) (8.3 mg, 20 µmol, 0.1 mol %) obtained in Example 9 and bis(2-methallyl)(1,5-cyclooctadiene)ruthenium ([Ru(methylallyl)$_2$(cod)]) (6.4 mg, 20 µmol, 0.1 mol %) successively, and the inside of the flask was evacuated and filled with nitrogen gas. Subsequently, dehydrated IPA (2.0 mL) was charged into the flask, and the mixture was stirred with a magnetic stirrer at 60° C. for 1 hour, and cooled to room temperature to prepare a catalyst solution. On the other hand, the inside of a 100 mL stainless steel-made autoclave apparatus equipped with a glass-made inner tube and a magnetic stirring bar was purged with nitrogen gas. Subsequently, acetophenone (2.33 mL, 20 mmol, 1.0 equivalent), dehydrated IPA (8.0 mL) and a catalyst solution prepared above (2.0 mL) were charged into the apparatus successively. Furthermore, the inside of the apparatus was replaced by hydrogen gas and the hydrogen pressure was set to 2 MPa, followed by stirring with a magnetic stirrer at 60° C. for 5 hours to produce target (S)-2-phenylethylalcohol. Conversion: >99%, selectivity: >99%, optical purity: 55.4% ee (according to GC analysis). Measurement conditions and GC retention time of the compound in GC analysis refer to Example 21.

While the present invention has been described in detail and with reference to specific embodiments thereof, it will be apparent to one skilled the art that various changes and modifications can be made therein without departing from the spirit and scope of the present invention. This application is based on Japanese Patent Application (Patent Application No. 2018-021749) filed on Feb. 9, 2018, the contents of which are incorporated herein by way of reference.

INDUSTRIAL APPLICABILITY

The compound (1$^A$) of the present invention can be synthesized conveniently by reacting the intermediate (2$^A$)

and the compound represented by the general formula (3). Further, a transition metal complex having the compound ($1^A$) of the present invention as a ligand exhibits excellent catalytic activity in various organic synthesis reactions. For example, the iron complex of the compound ($1^A$) of the present invention exhibits excellent asymmetry induction ability in the asymmetric transfer hydrogenation reaction of ketones, and the ruthenium complex of the compound ($1^A$) of the present invention exhibits high catalytic activity in the hydrogenation reaction of esters and the asymmetric hydrogenation reaction of ketones. By these reactions, it is possible to efficiently produce primary alcohols and optically active secondary alcohols that have an industrially high value.

The invention claimed is:

1. A compound represented by the following general formula ($1^A$):

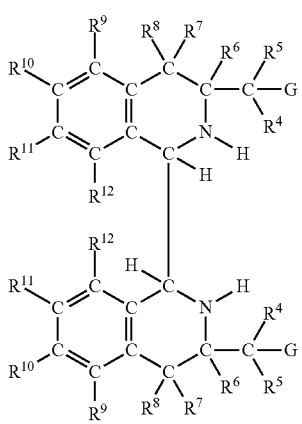

wherein in the formula ($1^A$), a solid line represents a single bond, a double line represents a double bond, C represents a carbon atom, H represents a hydrogen atom, N represents a nitrogen atom, and G represents a group selected from the group consisting of a monovalent group represented by the following general formula ($G^P$):

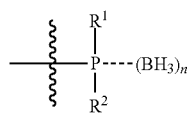

wherein in the formula ($G^P$), a solid line represents a single bond, a broken line represents a coordinate bond, a solid line intersected with a wavy line represents a bond to a carbon atom, P represents a phosphorus atom, $BH_3$ represents a boron trihydride, a subscript n represents a coordination number of $BH_3$ to P and indicates an integer value of 0 or 1, $R^1$ and $R^2$ each independently represent a group selected from the group consisting of an alkyl group, a cycloalkyl group, an alkenyl group which may have a substituent, an aryl group which may have a substituent, a heteroaryl group which may have a substituent, and an aralkyl group which may have a substituent, and $R^1$ and $R^2$ may bond to each other to form a ring which may have a substituent; and a monovalent group represented by the following general formula ($G^S$):

wherein in the formula ($G^S$), a solid line represents a single bond, a solid line intersected with a wavy line represents a bond to a carbon atom, S represents a sulfur atom, $R^3$ represents a group selected from the group consisting of an alkyl group, an alkenyl group which may have a substituent, an aryl group which may have a substituent, a heteroaryl group which may have a substituent, and an aralkyl group which may have a substituent; and wherein $R^4$, $R^5$, $R^6$, $R^7$, $R^8$, $R^9$, $R^{10}$, $R^{11}$ and $R^{12}$ each independently represent a hydrogen atom or a group selected from the group consisting of an alkyl group, an alkenyl group, an aryl group, an aralkyl group, an alkoxy group, a halogeno group, and a halogenoalkyl group.

2. The compound according to claim 1, wherein all of the $R^4$ to $R^{12}$ are hydrogen atoms.

3. The compound according to claim 2, wherein G is $G^P$.

4. The compound according to claim 3, which is an optically active substance.

5. A method for producing the compound according to claim 1, comprising reacting a compound represented by the following general formula ($2^A$):

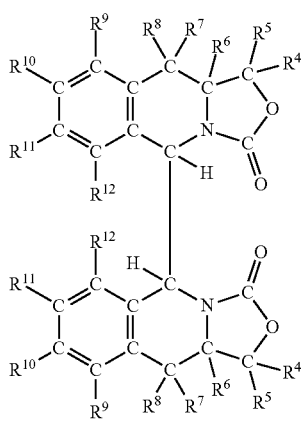

wherein in the formula ($2^A$), a solid line represents a single bond, a double line represents a double bond, C represents a carbon atom, H represents a hydrogen atom, N represents a nitrogen atom, O represents an oxygen atom, and $R^4$, $R^5$, $R^6$, $R^7$, $R^8$, $R^9$, $R^{10}$, $R^{11}$, and $R^{12}$ each independently represent a hydrogen atom or a group selected from the group consisting of an alkyl group, an alkenyl group, an aryl group, an aralkyl group, an alkoxy group, a halogeno group, and a halogenoalkyl group;

with a compound represented by the following general formula (3):

    (3)

wherein in the formula (3), a solid line represents a single bond, H represents a hydrogen atom, and G represents a group selected from the group consisting of a monovalent group represented by the following general formula ($G^P$):

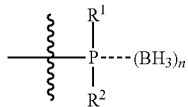    $G^P$ wherein in the formula ($G^P$), a solid line represents a single bond, a broken line represents a coordinate bond, a solid line intersected with a wavy line represents a bond to a carbon atom, P represents a phosphorus atom, $BH_3$ represents boron trihydride, a subscript n represents a coordination number of $BH_3$ to P and indicates an integer value of 0 or 1, $R^1$ and $R^2$ each independently represent a group selected from the group consisting of an alkyl group, a cycloalkyl group, an alkenyl group which may have a substituent, an aryl group which may have a substituent, a heteroaryl group which may have a substituent, and an aralkyl group which may have a substituent, and $R^1$ and $R^2$ bond to each other to form a ring which may have a substituent; and a monovalent group represented by the following general formula ($G^S$):

    $G^S$ wherein in the formula ($G^S$), a solid line represents a single bond, a solid line intersected with a wavy line represents a bond to a carbon atom, S represents a sulfur atom, $R^3$ represents a group selected from the group consisting of an alkyl group, an alkenyl group which may have a substituent, an aryl group which may have a substituent, a heteroaryl group which may have a substituent, and an aralkyl group which may have a substituent.

6. A transition metal complex comprising the compound according to claim 1 as a ligand.

7. The transition metal complex according to claim 6, having a metal species that is selected from the group consisting of transition metals of Group 8 to 11.

8. The transition metal complex according to claim 7, wherein the metal species is a metal species selected from the transition metals of Group 8.

* * * * *